(12) United States Patent
Podmore et al.

(10) Patent No.: US 7,678,109 B2
(45) Date of Patent: Mar. 16, 2010

(54) ABLATION DEVICE AND METHOD COMPRISING MOVABLE ABLATION ELEMENTS

(75) Inventors: Jonathan L. Podmore, San Carlos, CA (US); Michael Holzbaur, East Palo Alto, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 333 days.

(21) Appl. No.: 11/642,821

(22) Filed: Dec. 21, 2006

(65) Prior Publication Data

US 2007/0299436 A1    Dec. 27, 2007

Related U.S. Application Data

(60) Provisional application No. 60/815,881, filed on Jun. 23, 2006.

(51) Int. Cl.
*A61B 18/18* (2006.01)

(52) U.S. Cl. .......................................... 606/41; 607/122

(58) Field of Classification Search .................. 606/41, 606/45–50; 607/101, 102, 122
See application file for complete search history.

(56) References Cited

U.S. PATENT DOCUMENTS

| 5,192,280 | A | * | 3/1993 | Parins .......................... 606/48 |
| 5,263,493 | A | * | 11/1993 | Avitall ......................... 607/122 |
| 5,295,484 | A | | 3/1994 | Marcus et al. |
| 5,462,545 | A | | 10/1995 | Wang et al. |
| 5,575,766 | A | | 11/1996 | Swartz et al. |
| 5,582,609 | A | | 12/1996 | Swanson et al. |
| 5,590,657 | A | | 1/1997 | Cain et al. |
| 5,722,402 | A | | 3/1998 | Swanson et al. |
| 5,735,280 | A | | 4/1998 | Sherman et al. |
| 5,782,828 | A | | 7/1998 | Chen et al. |
| 5,788,636 | A | | 8/1998 | Curley |
| 5,916,213 | A | | 6/1999 | Haissaguerre et al. |
| 5,971,983 | A | | 10/1999 | Lesh |
| 6,007,499 | A | | 12/1999 | Martin et al. |
| 6,012,457 | A | | 1/2000 | Lesh |
| 6,142,993 | A | | 11/2000 | Whayne et al. |
| 6,235,024 | B1 | | 5/2001 | Tu et al. |
| 6,245,061 | B1 | | 6/2001 | Panescu et al. |
| 6,251,128 | B1 | | 6/2001 | Knopp et al. |
| 6,440,128 | B1 | * | 8/2002 | Edwards et al. ............... 606/41 |
| 6,605,084 | B2 | | 8/2003 | Acker et al. |
| 6,645,199 | B1 | | 11/2003 | Jenkins et al. |
| 6,689,128 | B2 | * | 2/2004 | Sliwa et al. ................... 606/41 |
| 6,814,732 | B2 | * | 11/2004 | Schaer ........................ 606/41 |

(Continued)

*Primary Examiner*—Michael Peffley
(74) *Attorney, Agent, or Firm*—Wiley Rein LLP

(57) ABSTRACT

A device for ablating tissue includes an elongate body, which may be flexible to wrap about a cardiac structure, and at least one movable ablation element coupled to the body. The movable ablation element is adjustable relative to the body to form an angle with a longitudinal axis thereof between about zero degrees and about 180 degrees. The movable ablation element may be a two element array, and a pivot pin may depend from an underside thereof to pivotably connect the array to the body via a mating pivot hole in the body. The body may be formable into both a substantially flat configuration and a generally curved configuration. In other embodiments, the body is wand-shaped. The device may further include at least one non-movable ablation element coupled to the body and forming an angle of about zero degrees with the longitudinal axis of the body.

8 Claims, 18 Drawing Sheets

U.S. PATENT DOCUMENTS 6,939,349 B2 * 9/2005 Fleischman et al. ........... 606/41
6,971,394 B2 12/2005 Sliwa et al.
7,052,493 B2 5/2006 Vaska et al.
2004/0162551 A1 * 8/2004 Brown et al. .................. 606/41

* cited by examiner

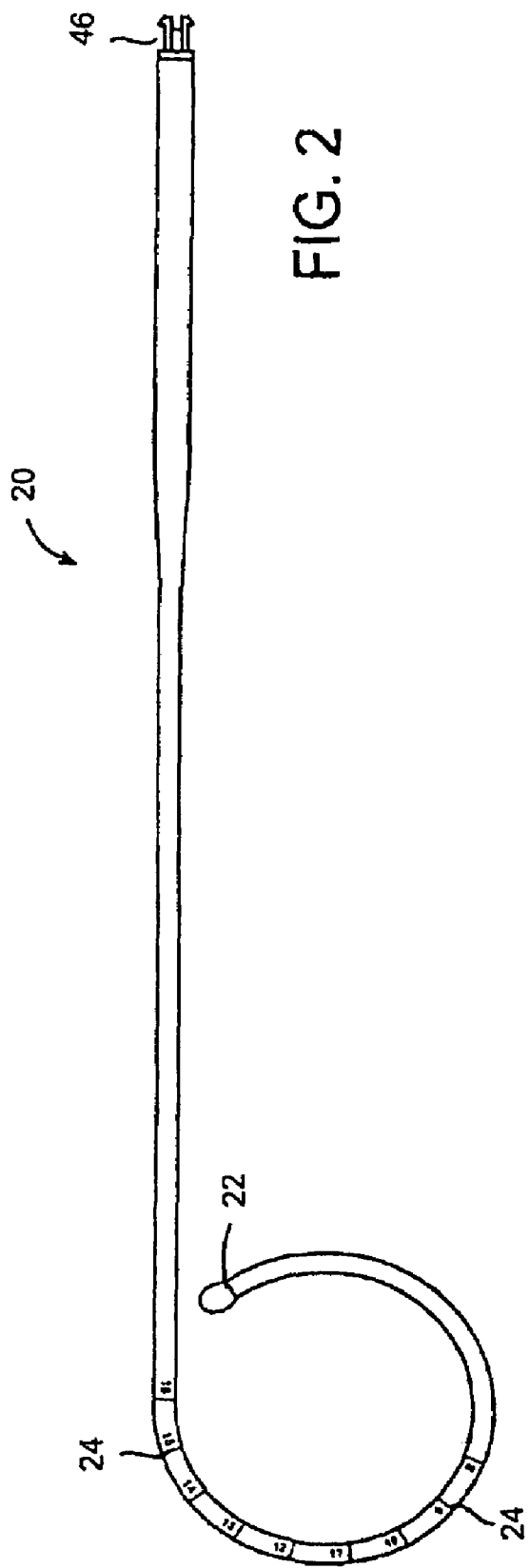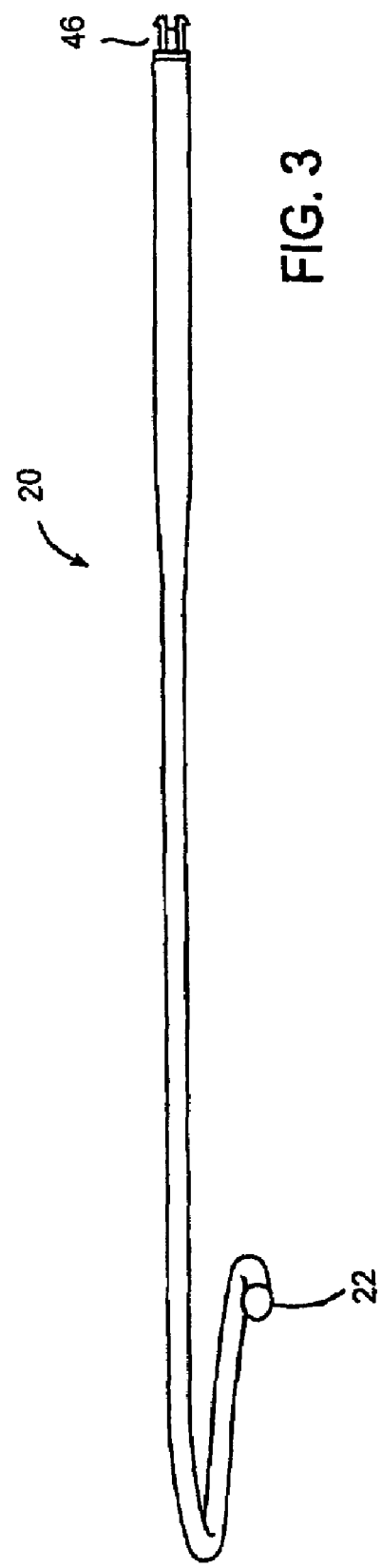

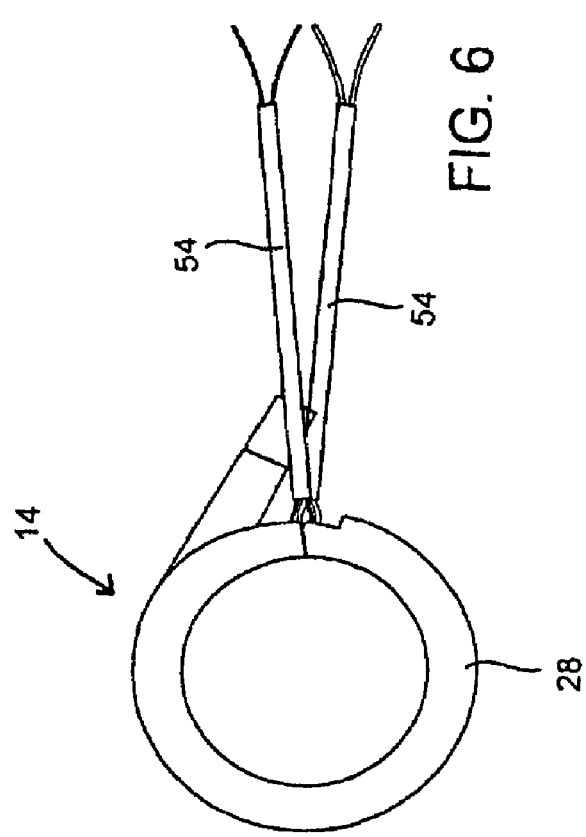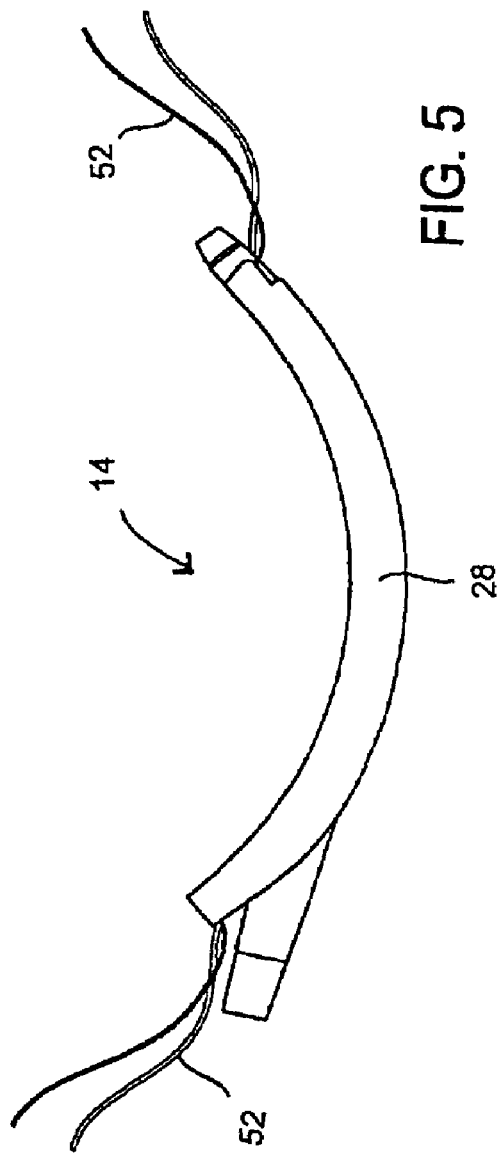

ABLATION DEVICE AND METHOD COMPRISING MOVABLE ABLATION ELEMENTS

CROSS-REFERENCE TO RELATED APPLICATIONS

This application claims the benefit of U.S. provisional application No. 60/815,881, filed 23 Jun. 2006, which is hereby incorporated by reference as though fully set forth herein.

This application is related to U.S. provisional application No. 60/815,852, U.S. provisional application No. 60/815,853, U.S. provisional application No. 60/815,880, and U.S. provisional application No. 60/815,882, all filed 23 Jun. 2006. All of the foregoing applications are hereby incorporated by reference as though fully set forth herein.

BACKGROUND OF THE INVENTION a. Field of the Invention

The instant invention generally relates to devices and methods for treating electrophysiological diseases of the heart. In particular, the instant invention relates to devices and methods for epicardial ablation for the treatment of atrial fibrillation.

b. Background Art

It is well known that atrial fibrillation results from disorganized electrical activity in the heart muscle (the myocardium). The surgical maze procedure has been developed for treating atrial fibrillation, and involves the creation of a series of surgical incisions through the atrial myocardium in a preselected pattern so as to create conductive corridors of viable tissue bounded by scar tissue.

As an alternative to the surgical incisions of the maze procedure, transmural ablations of the heart may be used. Such ablations may be performed either from within the chambers of the heart (endocardial ablation), using endovascular devices (e.g., catheters) introduced through arteries or veins, or from outside the heart (epicardial ablation) using devices introduced into the patient's chest. Various ablation techniques may be used, including, but not limited to, cryogenic ablation, radio frequency (RF) ablation, laser ablation, ultrasonic ablation, and microwave ablation. The ablation devices are used to create elongated transmural lesions—that is, lesions extending through a sufficient thickness of the myocardium to block electrical conduction—forming the boundaries of the conductive corridors in the atrial myocardium. Perhaps most advantageous about the use of transmural ablation rather than surgical incision is the ability to perform ablation procedures without first establishing cardiopulmonary bypass (CPB).

In performing the maze procedure and its variants, whether using ablation or surgical incisions, it is generally considered most efficacious to include a transmural incision or lesion isolating the pulmonary veins from the surrounding myocardium. The pulmonary veins connect the lungs to the left atrium of the heart, joining the left atrial wall on the posterior side of the heart. Such procedures have been found to offer 57% to 70% success without antiarrhythmic drugs. However, they are also associated with a 20% to 60% recurrence rate as the result of lesion recovery, non-pulmonary vein foci of the arrhythmia, or the need for further tissue modifications.

Previous surgical and catheter-based approaches have demonstrated that linear left atrial (LA) lesions were successful in treating atrial fibrillation when complete block was achieved. One such technique involves linear ablation at the mitral isthmus, which is defined as extending from the lateral mitral annulus to the ostium of the left inferior pulmonary vein (LIPV). Studies have shown that catheter ablation of the mitral isthmus, in combination with pulmonary vein (PV) isolation, consistently results in demonstrable conduction block and is associated with a high cure rate for paroxysmal atrial fibrillation.

Producing precise lesions at these locations presents significant obstacles for the physician performing endocardial ablations for several reasons. First, while many of the lesions created in the maze procedure can be created from within the right atrium, the pulmonary venous lesions must be created in the left atrium, requiring either a separate atrial access point or a transseptal puncture from the right atrium. Second, the elongated and flexible endovascular ablation devices are difficult to manipulate into the complicated geometries required for forming the pulmonary venous lesions. It is also difficult maintain proper positioning of the ablation device against the wall of a beating heart. Furthermore, visualization of endocardial anatomy and endovascular devices is often inadequate, such that knowing the precise position of an endovascular device can be difficult, potentially resulting in misplaced lesions.

Epicardial ablation devices and methods useful for creating transmural lesions for the treatment of atrial fibrillation have been described in U.S. Pat. No. 7,052,493 to Vaska et al. ("Vaska") and U.S. Pat. No. 6,971,394 to Sliwa et al. ("Sliwa"), both of which are hereby expressly incorporated by reference as though fully set forth herein. Sliwa describes a method of forming a transmural lesion in a wall of the heart adjacent to the pulmonary veins by placing an ablation device through a thoracic incision, and then through a pericardial penetration, so that the ablation device is disposed in contact with an epicardial surface of the heart. The ablation device includes a locating device, such as a catch, a branch, or a notch, near the working end of the catheter that is configured to engage one or more of the pulmonary veins or another nearby anatomical structure (e.g., a pericardial reflection, the inferior vena cava, the superior vena cava, the aorta, the left or right atrial appendage) in order to position the working end of the catheter adjacent to the pulmonary veins.

In order to take full advantage of the synergistic benefits of combining linear left atrial ablations such as the mitral isthmus ablation with PV isolation, it is important that the lesions have continuity with each other. Failure to provide continuity may allow for reentry pathways, which would limit the effectiveness of the treatment. Execution of a contiguous mitral isthmus ablation following PV isolation, however, presents considerable challenges to the physician. Difficulties in visualizing the precise location of a preexisting PV isolation ablation, compounded with the challenges of maintaining accurate placement on a beating heart, mean that a high degree of physician skill and experience are required in order to successfully create contiguous ablations.

BRIEF SUMMARY OF THE INVENTION

It is therefore desirable to provide a device that facilitates the creation of mitral isthmus ablations that are contiguous with PV isolation ablations.

According to a first embodiment of the present invention, a device for ablating tissue includes an elongate, flexible body configured to wrap about a cardiac structure and at least one movable ablation element coupled to the body, wherein the at least one movable ablation element is adjustable relative to the body to form an angle with a longitudinal axis of the body between about zero degrees and about ninety degrees. The at least one movable ablation element may be pivotably coupled to the body. Optionally, the at least one movable ablation element may be a two element array, and a pivot pin may depend from an underside of the two element array and pivotably connect the two element array to the body via a mating pivot hole in the body. In some embodiments of the invention, the body is formable into both a substantially flat configuration and a generally curved configuration, with the body in a generally curved configuration when in a relaxed state. The device may further include at least one non-movable ablation element coupled to the body and forming an angle of about zero degrees with the longitudinal axis of the body. To manipulate the at least one movable ablation element into the angled position, the device may include at least one control cable coupled to the at least one movable ablation element.

According to another aspect of the present invention, a method of ablating tissue includes the steps of: wrapping an ablation device having an elongate, flexible body and at least one movable ablation element about a cardiac structure; moving the at least one movable ablation element into such that it forms an angle between about zero degrees and about ninety degrees with a longitudinal axis of said body; and ablating tissue by supplying ablating energy to the at least one movable element. The step of wrapping an ablation device having an elongate, flexible body and at least one movable ablation element about a cardiac structure optionally includes wrapping the ablation device about the cardiac structure such that it overlaps an existing ablation lesion, such as a PV isolation lesion. The ablation device may be introduced into a patient by coupling the ablation device to a trailing edge of a PV isolation lesion ablation device and pulling on a leading edge of the PV isolation lesion ablation device.

In yet another aspect of the present invention, a method of manufacturing a device for ablating tissue includes the steps of: providing an elongate, flexible body; providing at least one ablation element; and movably coupling the at least one ablation element to the body such that the at least one ablation element can be moved to form an angle of between about zero degrees and about ninety degrees with a longitudinal axis of said body.

In still another embodiment of the invention, a device for ablating tissue includes an elongate, flexible body and a plurality of ablation elements coupled to said body and substantially aligned along a common axis of said body, wherein a subset of the plurality of ablation elements is movable into an angled position relative to said common axis. The subset is optionally coupled to the body via a pivot pin. At least one control cable may be coupled to the subset of ablation elements and configured to move the subset of the plurality of ablation elements into the angled position. When the subset is moved into the angled position, it may be located to create an ablation lesion that is substantially contiguous with an ablation lesion created by the plurality of ablation elements.

According to still a further aspect of the present invention, a method of ablating tissue includes the steps of: securing a plurality of ablation elements about at least a portion of a circumference of a heart; activating the plurality of ablation elements to create a substantially continuous elongate lesion; controlling a movement of at least one of the plurality of ablation elements to adjust an angle of the movement relative to an axis of the elongate lesion; and activating the at least one of the plurality of ablation elements to create a lesion contiguous with and angled relative to the elongate lesion. Optionally, the step of controlling a movement of at least one of the plurality of ablation elements to adjust an angle of the movement relative to an axis of the elongate lesion comprises adjusting the angle to at least about 45°, and preferably about 90°.

According to yet another embodiment of the invention, a device for ablating tissue includes an elongate shaft having a distal end and at least one ablation element movably coupled to the distal end of the shaft, wherein the at least one ablation element is adjustable relative to the shaft to form an angle with a longitudinal axis of the shaft between about zero degrees and about ninety degrees.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 2 shows an introducer.

FIG. 3 is a side view of the introducer illustrated in FIG. 2.

FIG. 5 illustrates the ablation device of FIG. 4 in an open position.

FIG. 6 shows the ablation device of FIG. 4 forming a closed loop.

DETAILED DESCRIPTION OF THE INVENTION

Figure 1:
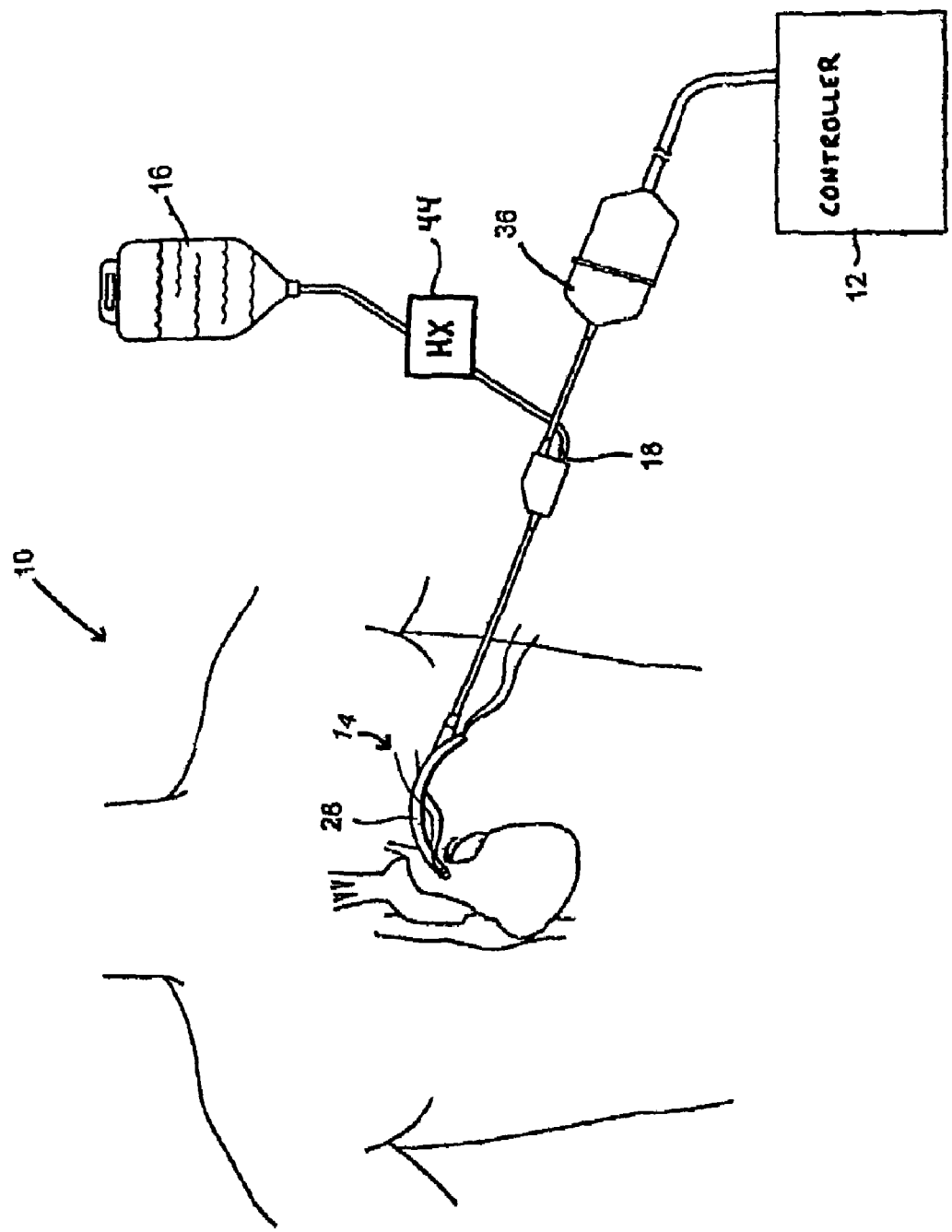
FIG. 1 schematically illustrates an ablation system according to an embodiment of the present invention.

Referring now to FIG. 1, an ablation system 10 according to one embodiment of the present invention is shown. Ablation system 10 includes a controller 12, which preferably operates to deliver focused ultrasound energy. Ablation system 10 may be used to wrap an ablation device 14 around the pulmonary veins at an epicardial location in order to create a pulmonary vein (PV) isolation ablation lesion. Ablation system 10 may further include a source 16 of a flowable material, which may be a bag of saline that provides a gravity feed to ablation device 14 via a standard luer connection 18.

Figure 7:
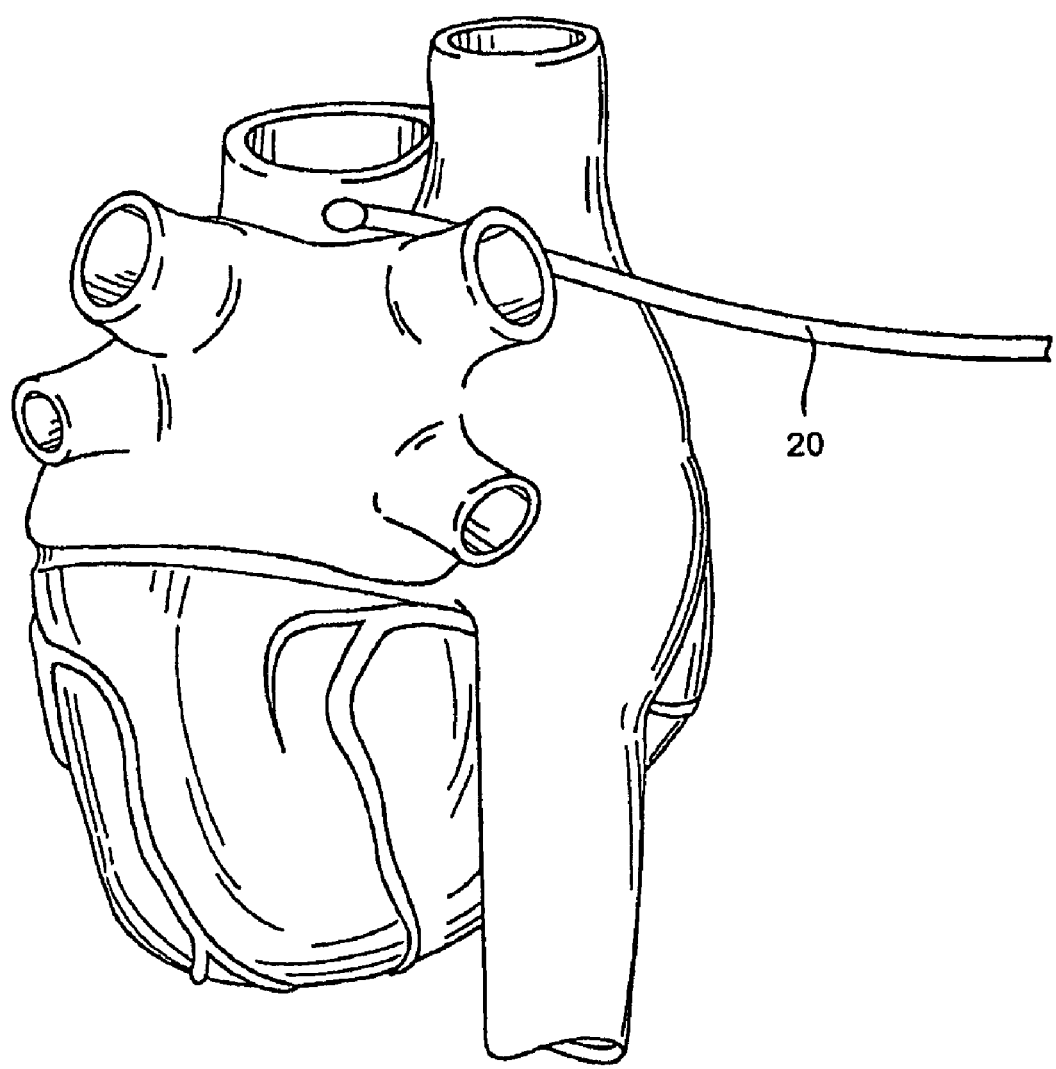
FIG. 7 illustrates the introducer of FIG. 2 being advanced around the pulmonary veins.
Figure 8:
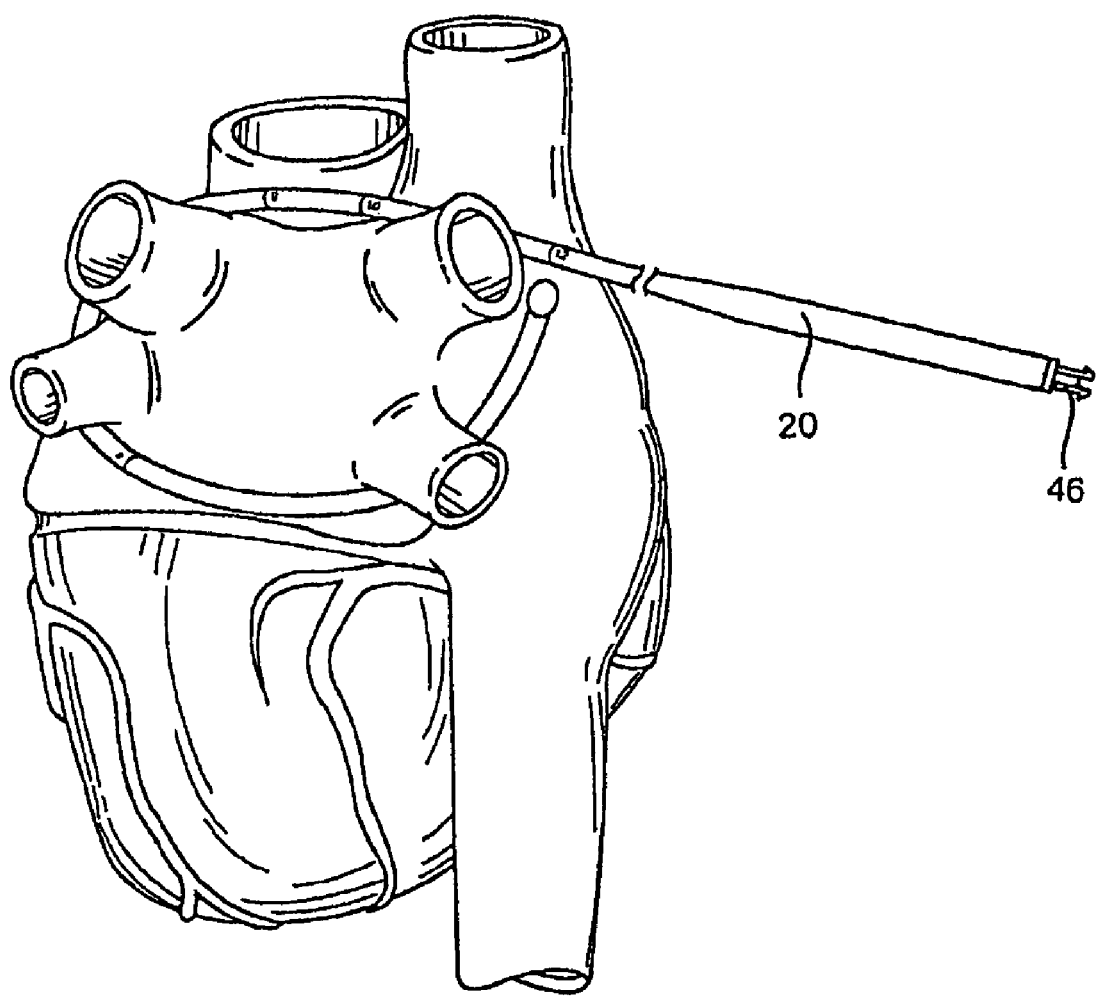
FIG. 8 depicts the introducer extending around the pulmonary veins in order to size an ablation device.

The system further includes an introducer 20, illustrated in FIGS. 2 and 3, which is advanced around the pulmonary veins as shown in FIGS. 7 and 8 and described below. As shown in FIG. 2, introducer 20 preferably forms a substantially closed loop in an unbiased configuration, with a small offset near its distal tip 22 as shown in FIG. 3.

Figure 4:
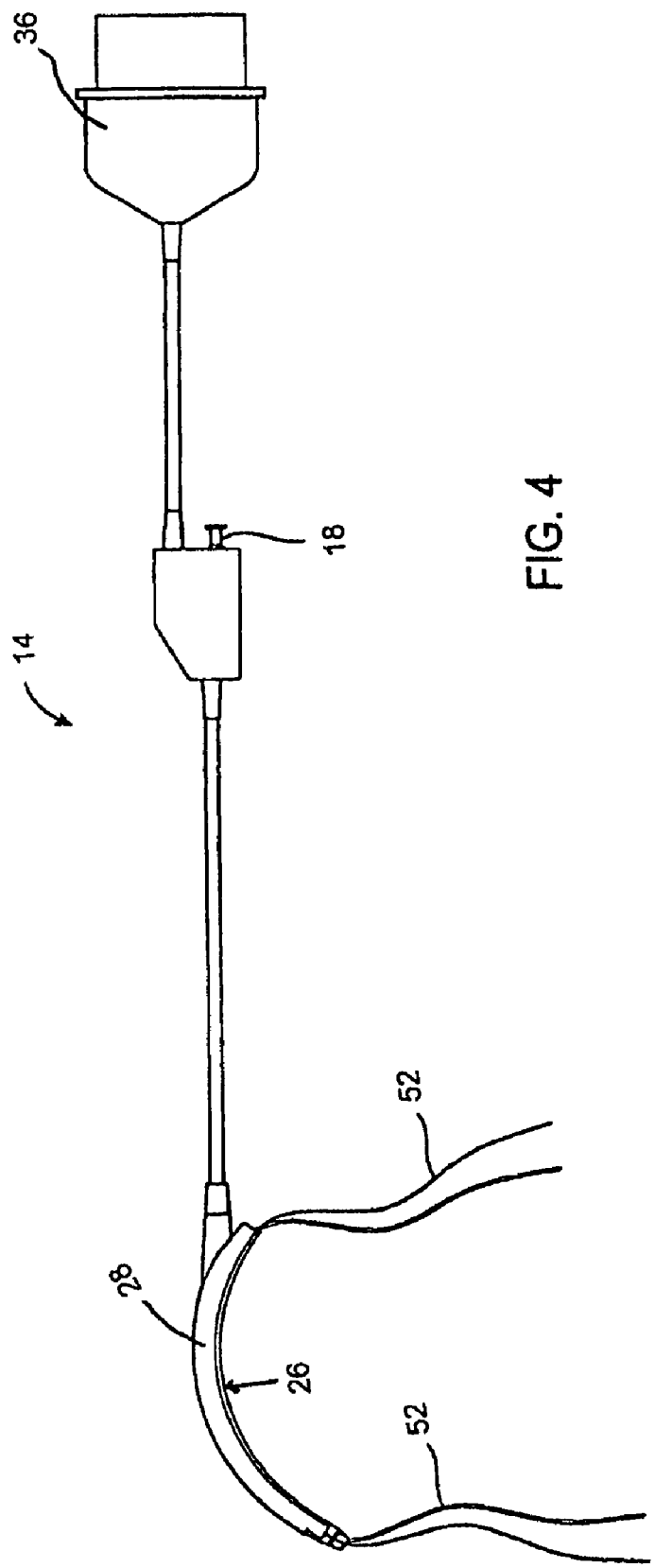
FIG. 4 illustrates an ablation device for creating PV isolation ablations.

Introducer 20 may be used as a sizing device for sizing ablation device 14. For example, as shown in FIG. 2, introducer 20 may have size indicators 24 usable to determine the appropriate size of ablation device 14. For ablation device 14 shown in FIGS. 4 through 6 and described in detail herein, the size of ablation device 14 is effectively determined by the number of ablation elements. It is also contemplated, however, that other methodologies for sizing ablation device 14 may be used without departing from the spirit and scope of the present invention.

In use, and as illustrated in FIGS. 7 and 8, introducer 20 is inserted into the patient and passed through an incision in the pericardial reflection adjacent the right superior pulmonary vein adjacent the transverse pericardial sinus. Introducer 20 is then advanced through the transverse pericardial sinus, around the left superior and inferior pulmonary veins, and out through another incision in the pericardial reflection near the right inferior pulmonary vein. The appropriate size of ablation device 14 may then be read using indicators 24 imprinted on introducer 20. For example, in FIG. 8, size indicators 24 of introducer 20 read "12," indicating that an ablation device 14 having 12 ablation elements will substantially encircle the pulmonary veins.

Figure 16:
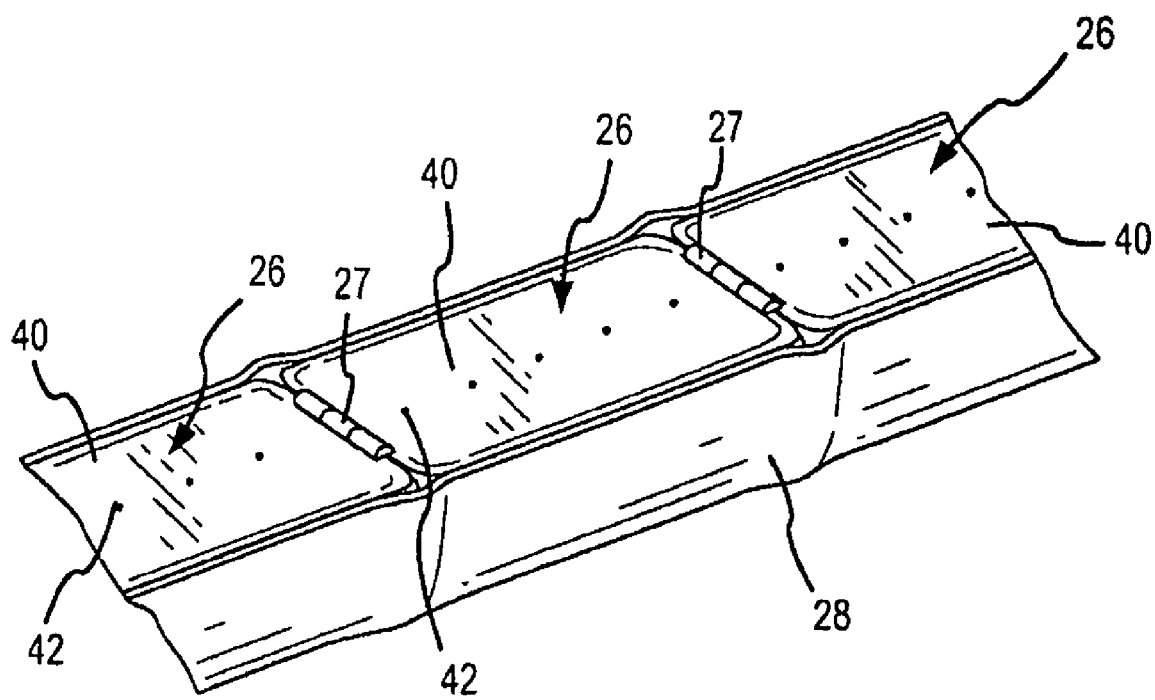
FIG. 16 is a magnified view of one segment of the ablation device of FIG. 4.
Figure 17:
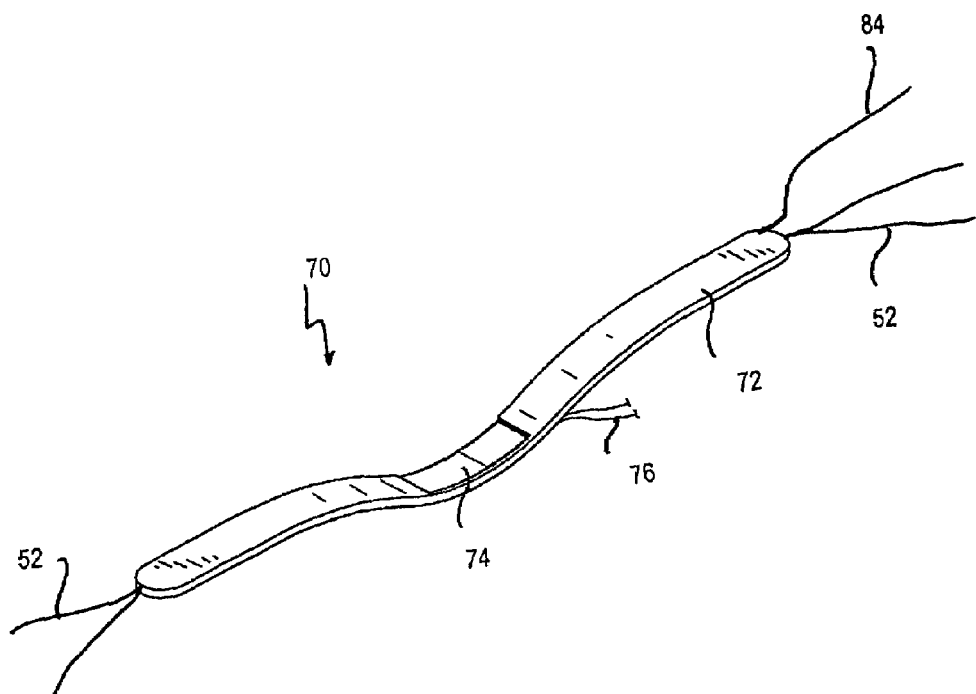
FIG. 17 shows an isometric view of an ablation device including movable ablation elements.
Figure 18:
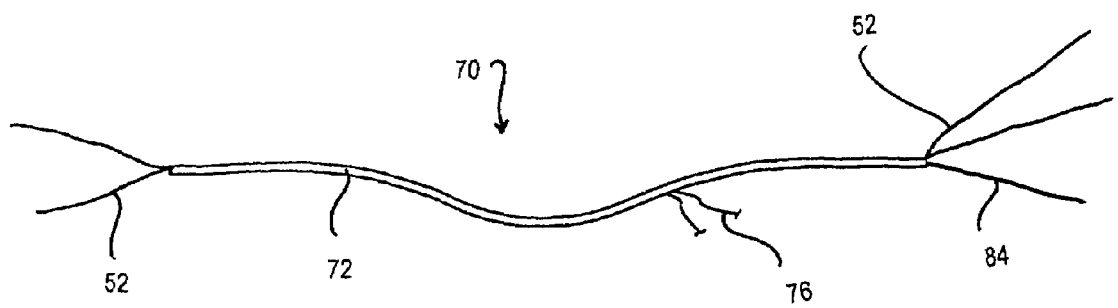
FIG. 18 is a side view of the ablation device of FIG. 17.

With reference to FIGS. 4-6 and 16, ablation device 14 includes a plurality of ablation elements 26 substantially aligned along a common axis and coupled together, preferably through integrally formed hinges 27 (as seen in FIG. 16) in ablation device 14. By "substantially aligned along a common axis," it is meant that there is little or no staggering between ablation elements 26 along the direction in which they are coupled together. It should be understood that ablation elements 26 may alternatively be coupled together with mechanical connections, rather than integrally formed hinges 27 without departing from the scope of the invention. Ablation device 14 preferably has from about 5 to about 30 ablation elements 26, more preferably from about 10 to about 25 ablation elements 26, and most preferably less than about 15 ablation elements 26. It should be understood, however, that any number of ablation elements 26 may be used depending upon the specific application for ablation device 14. For example, ablation device 14 may be used to extend around only a single vessel, such as the aorta, a pulmonary vein, the superior vena cava, or inferior vena cava, in which case ablation device 14 preferably includes about 4 to about 12 ablation elements 26, and more preferably includes about 8 ablation elements 26. Each ablation element 26 is preferably a discrete, autonomously controlled cell.

A body 28 of ablation device 14 is preferably made of a polymeric material such as polycarbonate, polyetherimide (e.g., Ultem®), silicone, or urethane, and is preferably formed by injection molding. One of ordinary skill will appreciate, however, that any suitable materials and methods may be used to form ablation device 14 without departing from the spirit and scope of the present invention. Preferably, an outer surface of body 28 is smooth in order to limit the risk of catching ablation device 14 on patient tissue or otherwise causing trauma during insertion of ablation device 14.

Figure 14:
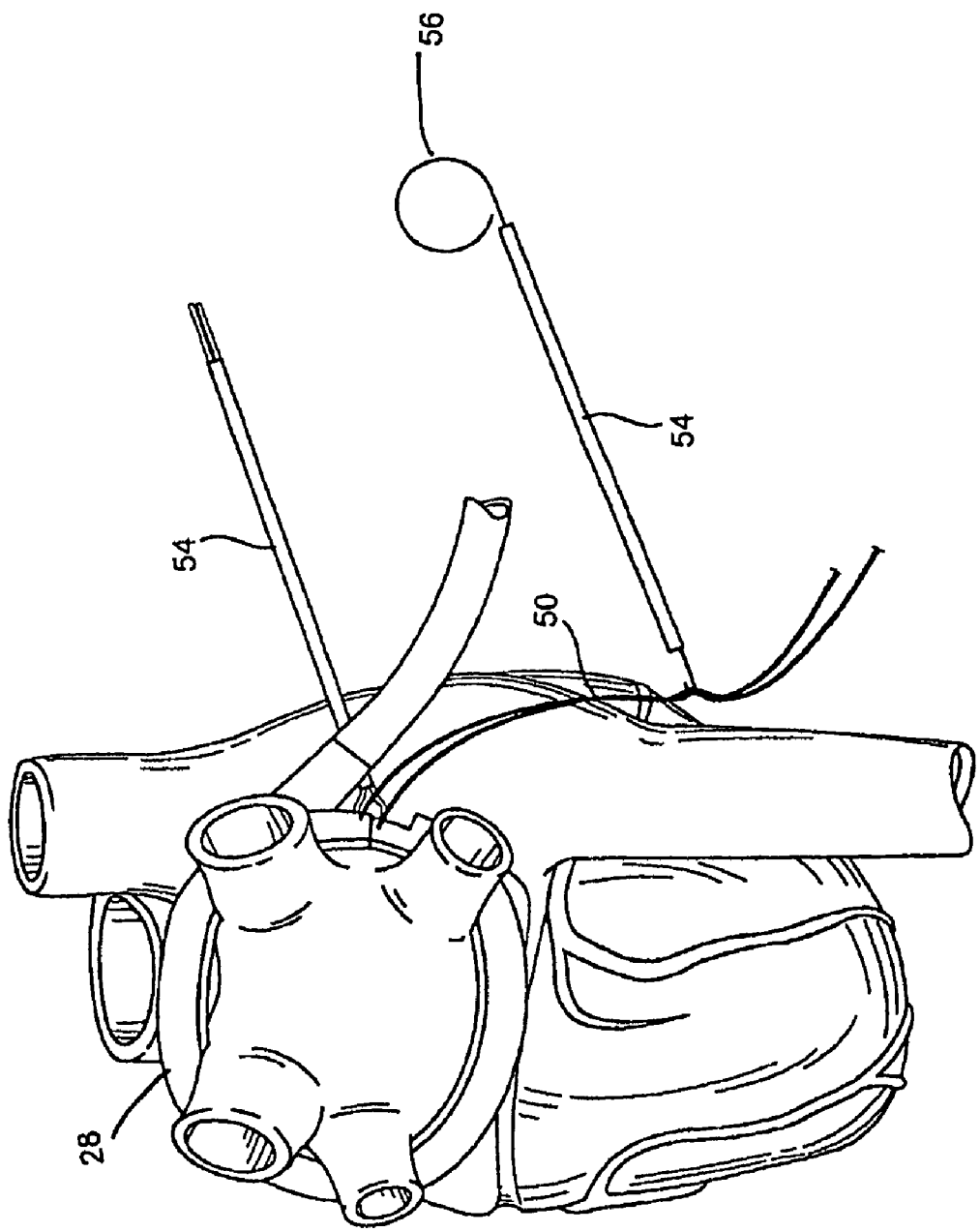
FIG. 14 depicts the ablation device forming a closed loop about the pulmonary veins.
Figure 15:
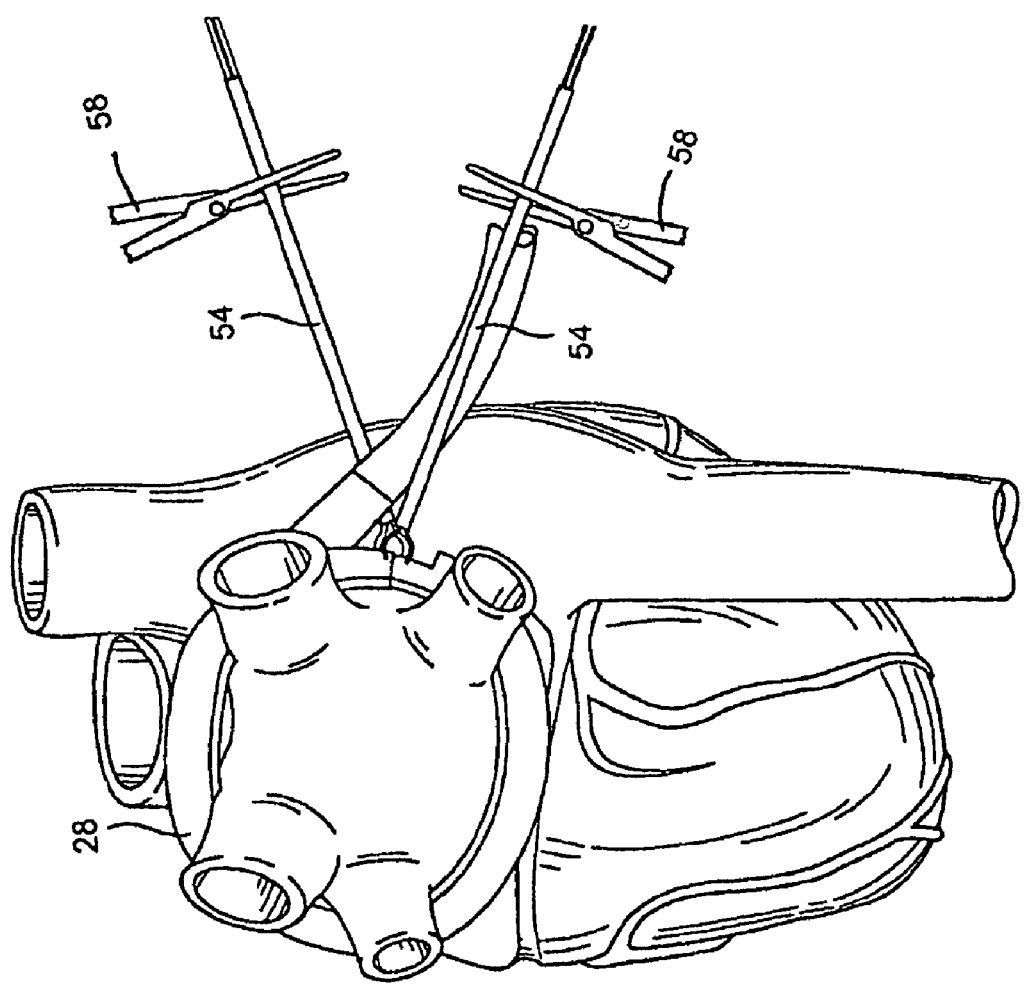
FIG. 15 depicts the ablation device forming a closed loop about the pulmonary veins and secured in this configuration using sutures.

Ablation device 14 is configured to have a predetermined curvature that facilitates encircling an area of the heart while simultaneously permitting ablation device 14 to be straightened or flattened to minimize the overall width thereof. The latter (i.e., flattened) configuration facilitates insertion of ablation device 14 through a relatively smaller incision in the patient in order to reach the heart tissue, and thus is referred to herein as an "insertion configuration." In other words, ablation device 14 is configured to permit at least two distinct configurations: a predetermined curvature (e.g., FIG. 5) to facilitate manipulation around the heart and a substantially straight, generally flattened shape (having little or no curvature) to facilitate insertion into the patient's body. By using the flattened configuration during insertion, the surgeon may use a smaller incision, which reduces the patient's recovery time. By using the curved configuration to manipulate ablation device 14 around the patient's heart, the surgeon is able to more easily maneuver ablation device 14 into position for treatment. Ablation device 14 may also be deformed into a third configuration, which is a generally closed loop as seen in FIGS. 6, 14, and 15. This third configuration will be described in further detail below.

The phrase "predetermined curvature" is intended to convey that ablation device 14 is designed to assume a curved shape and maintain that general shape during certain intended manipulations. For example, while ablation device 14 may be maintained in a substantially straightened position for insertion, ablation device 14 is intended to resume and maintain a curved shape during manipulation about the heart. Additional forces may be applied on ablation device 14 in order to increase or decrease the degree of curvature, for example into the substantially closed loop third configuration illustrated in FIG. 6. The use of "predetermined" is intended to convey that ablation device 14 maintains a generally curved shape while being positioned around a portion of the heart (that is, the "relaxed" state of ablation device 14, with no external forces applied thereto, is a generally curved configuration).

In one preferred embodiment of ablation device 14, ablation elements 26 are connected using a superelastic material, including, by way of example only, a memory metal such as Nitinol. As one of ordinary skill in the art will understand, a "superelastic material" is a type of shape memory alloy that does not require a temperature change in order to regain its original, undeformed shape. The superelastic properties allow ablation device 14 to be substantially deformed to become substantially coplanar and then to return to the predetermined curvature. For example, all ablation elements 26 may be interconnected using one or more strands of Nitinol, or another superelastic material, such that ablation device 14 may be substantially straightened for insertion into the patient through a relatively small incision, and thereafter manipulated into position about the heart in a generally curved configuration. The Nitinol or other superelastic material may take the form of a hinge wire that connects a plurality of ablation elements 26 to maintain the predetermined curvature.

In one embodiment, each ablation element 26 is contained in a housing, the edges of which may be angled to permit adjacent ablation elements to have at least two relationships to one another: one in which they are substantially coplanar, resulting in a substantially flat configuration, and another in which they are at an angle, resulting in a generally curved configuration. Preferably, the angle between the faces of adjacent ablation elements 26 when ablation device 14 is in its relaxed state (i.e., the generally curved configuration) may be adjusted based on the number of ablation elements 26, and may typically be between about 10 degrees and about 30 degrees. The hinges may be integrated wholly or partially into the housings.

It is also contemplated that the adjustable configurations of ablation elements 26 may be implemented utilizing a spring system, such as a combination of mechanical hinges and/or springs. The mechanical hinges and/or springs may be used in conjunction with ablation elements 26 having angled edges as described above. In addition, a standard guidewire structure, which generally includes a tightly coiled wire and, optionally, a core wire running therethrough, may be utilized to interconnect ablation elements 26 without departing from the spirit and scope of the present invention.

Optionally, ablation device 14 may be deformed temporarily during insertion of ablation device 14 into the patient with the assistance of a sheath. The sheath applies a deforming force to ablation device 14 and assists in maintaining ablation elements 26 in a substantially straight insertion configuration. Preferably, the sheath is a straight cylinder that is sized to accommodate ablation device 14 in the substantially straight insertion configuration. Thus, the sheath may be used to introduce ablation device 14 through an incision into the patient. Once ablation device 14 has been introduced through the incision, the sheath may be removed, and the tension caused by the superelastic wire or spring system will cause ablation device 14 to resume its predetermined curvature.

Alternatively, a stylet may be used to deform ablation device 14 into the generally straight insertion configuration. Each ablation element 26 may include a guide tube shaped to receive the stylet therethrough. The guide tube may be internal to each ablation element 26 or mounted to the exterior of ablation device 14. As the stylet passes through the guide tubes, it applies a deforming force to ablation device 14 and assists in maintaining ablation elements 26 in a substantially straight configuration to facilitate insertion of ablation device 14 through an incision into the patient. Once ablation device 14 has been introduced, the stylet may be withdrawn, at which time the restorative force caused by the superelastic wire or spring system will cause ablation device 14 to resume its predetermined curvature.

Ablation elements 26 may be any element for directing and delivering ablating energy to the cardiac tissue, including, but not limited to, focused ultrasound elements, radio frequency (RF) elements, laser elements, and microwave elements. Ablation elements 26 preferably have a width of about 1 mm to about 15 mm, and more preferably of about 10 mm, and a length of about 2 mm to about 25 mm, and more preferably of about 12 mm.

Ablation elements 26 are coupled to controller 12 via wires. The wires may be collectively incorporated into a plug 36 usable to couple ablation device 14 to controller 12 as shown in FIG. 1. Controller 12 controls ablation, for example in the manner described herein. A source of ablation energy (e.g., a signal generator) may be part of controller 12 or separate therefrom. One or more temperature sensors, preferably thermocouples or thermistors, are positioned within recesses in the inner and outer lips of ablation device 14 in order to measure temperature. The temperature sensors are also coupled to controller 12, for example via plug 36, for monitoring purposes and to provide temperature feedback for controlling the ablation process as described herein.

Each ablation element 26 may also have a membrane 40 that contains the flowable material within a fluid chamber to provide a conformable interface with the tissue to be ablated as seen in FIG. 16. Membrane 40 may include openings 42 through which the flowable material may leak or weep, and each membrane 40 may be fed by an individual inlet leading thereto.

The flowable material is preferably supplied at an average flow rate of at least about 0.24 cc/sec, more preferably at least about 0.50 cc/sec, and most preferably at least about 1.0 cc/sec to each ablation element 26, although lower or higher flow rates may be used. The flowable material is preferably delivered to the inlet of ablation device 14 at a set pressure that results in the desired average flow rate through ablation elements 26. The flowable material may be heated or cooled as desired or required by passing it through a heat exchanger 44 prior to delivery to the inlet of ablation device 14 (e.g., luer connection 18 as seen in FIG. 1). The flowable material is preferably delivered at a temperature of no more than about 40 degrees C., and more preferably at a temperature of no more than about 25 degrees C., to cool the tissue and/or ablation elements 26. A fluid permeable, porous structure, such as gauze, may be also positioned to hold the flowable material within the fluid chamber and prevent direct contact between ablation elements 26 and the tissue being ablated.

Figure 9:
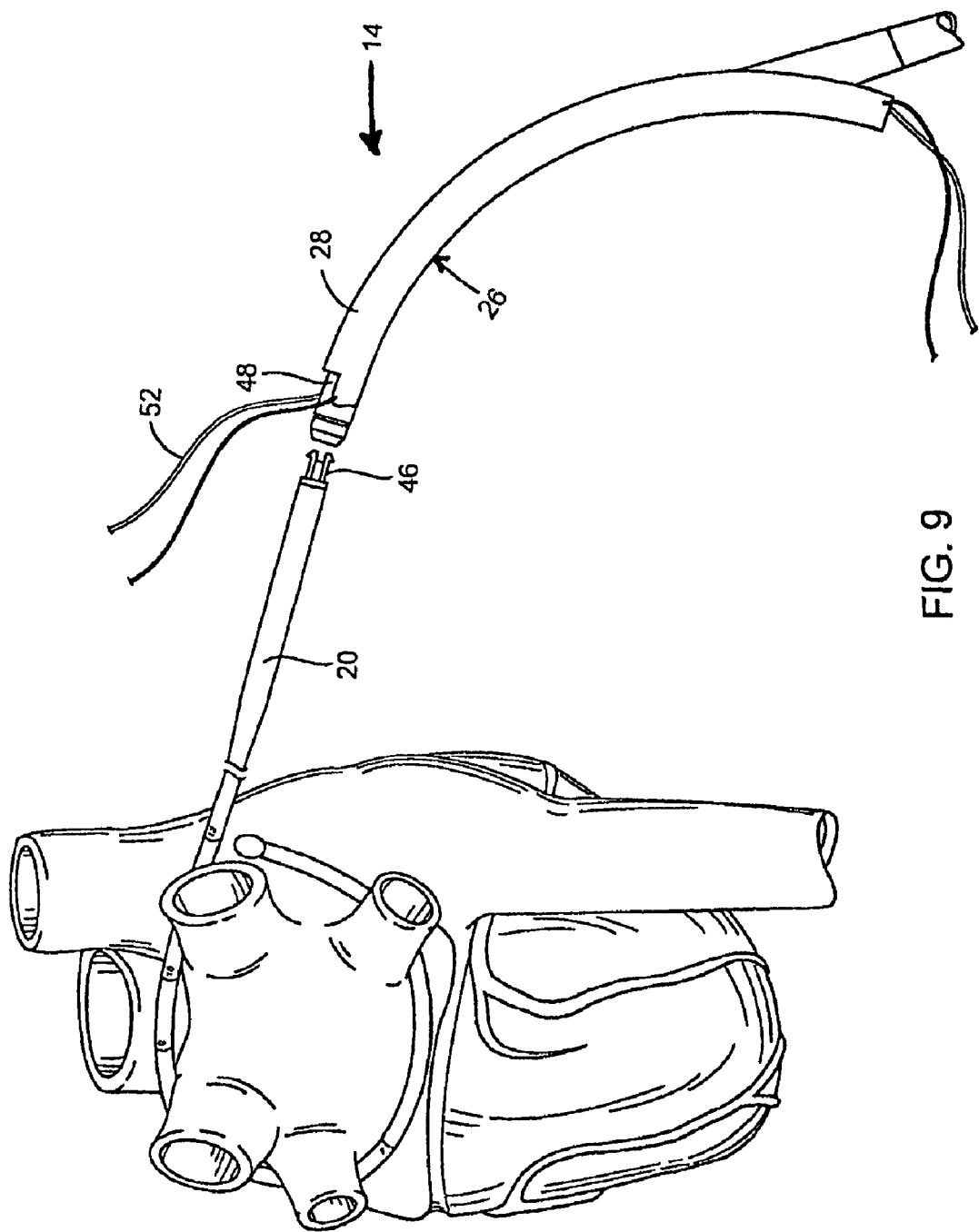
FIG. 9 shows the ablation device being connected to the introducer.
Figure 10:
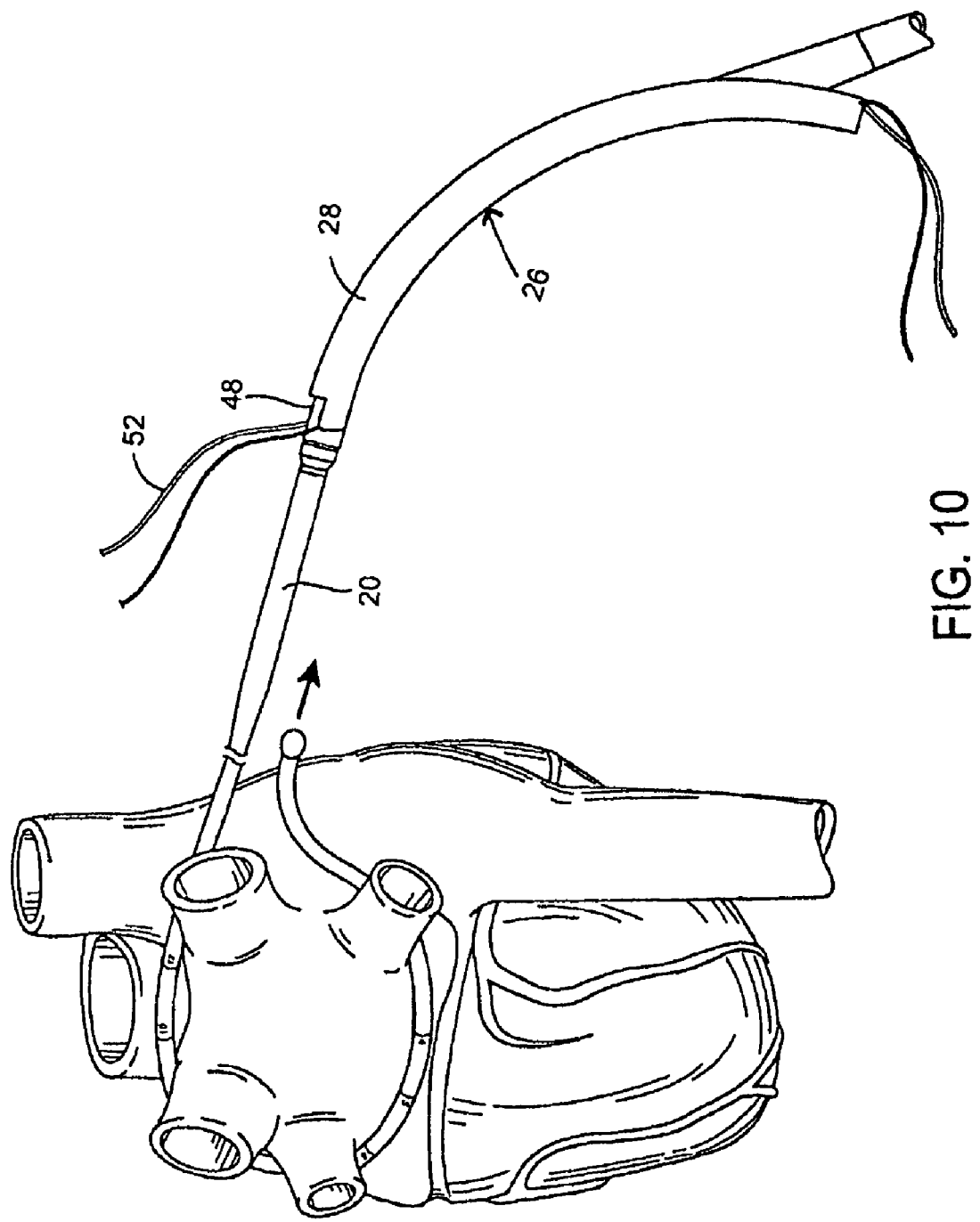
FIG. 10 illustrates the ablation device coupled to the introducer and being advanced around the pulmonary veins via manipulation of the introducer.
Figure 11:
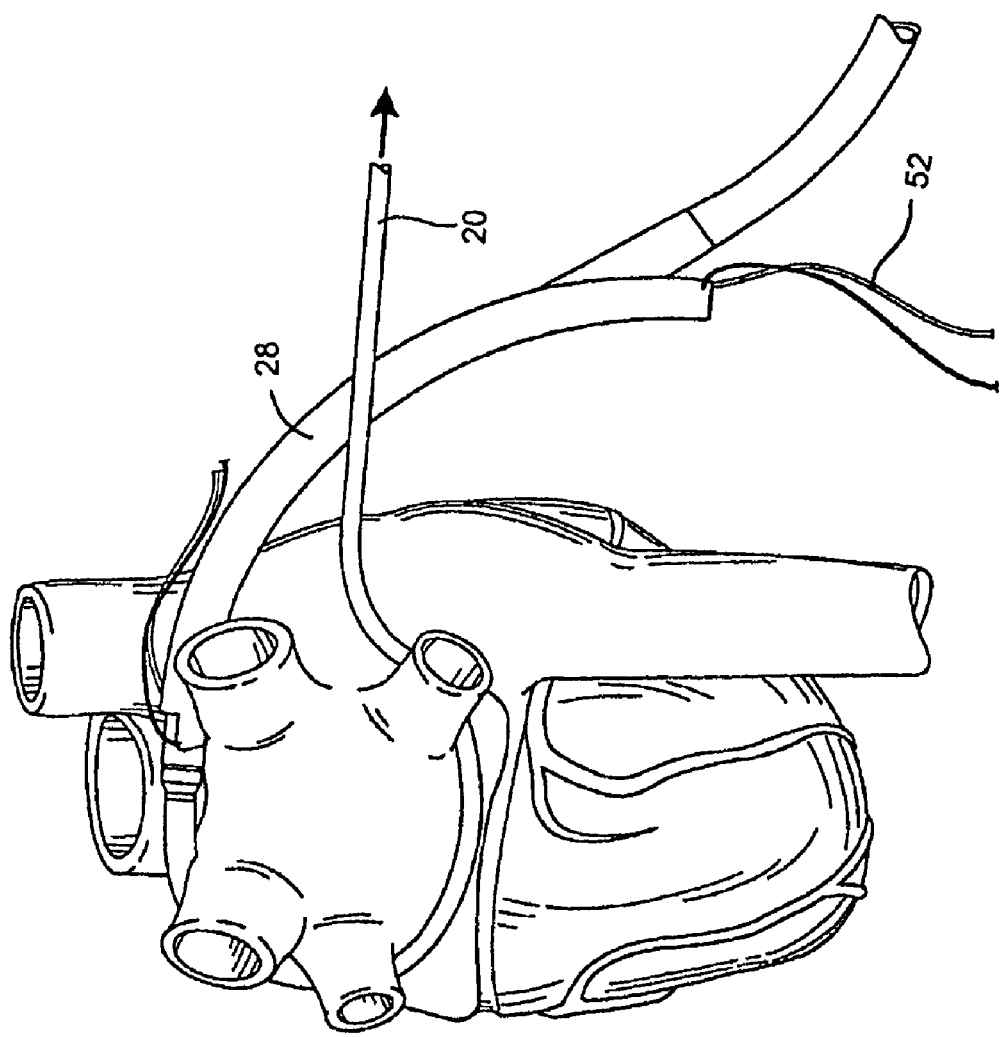
FIG. 11 illustrates the same thing as FIG. 10 at a later stage of the process.
Figure 13:
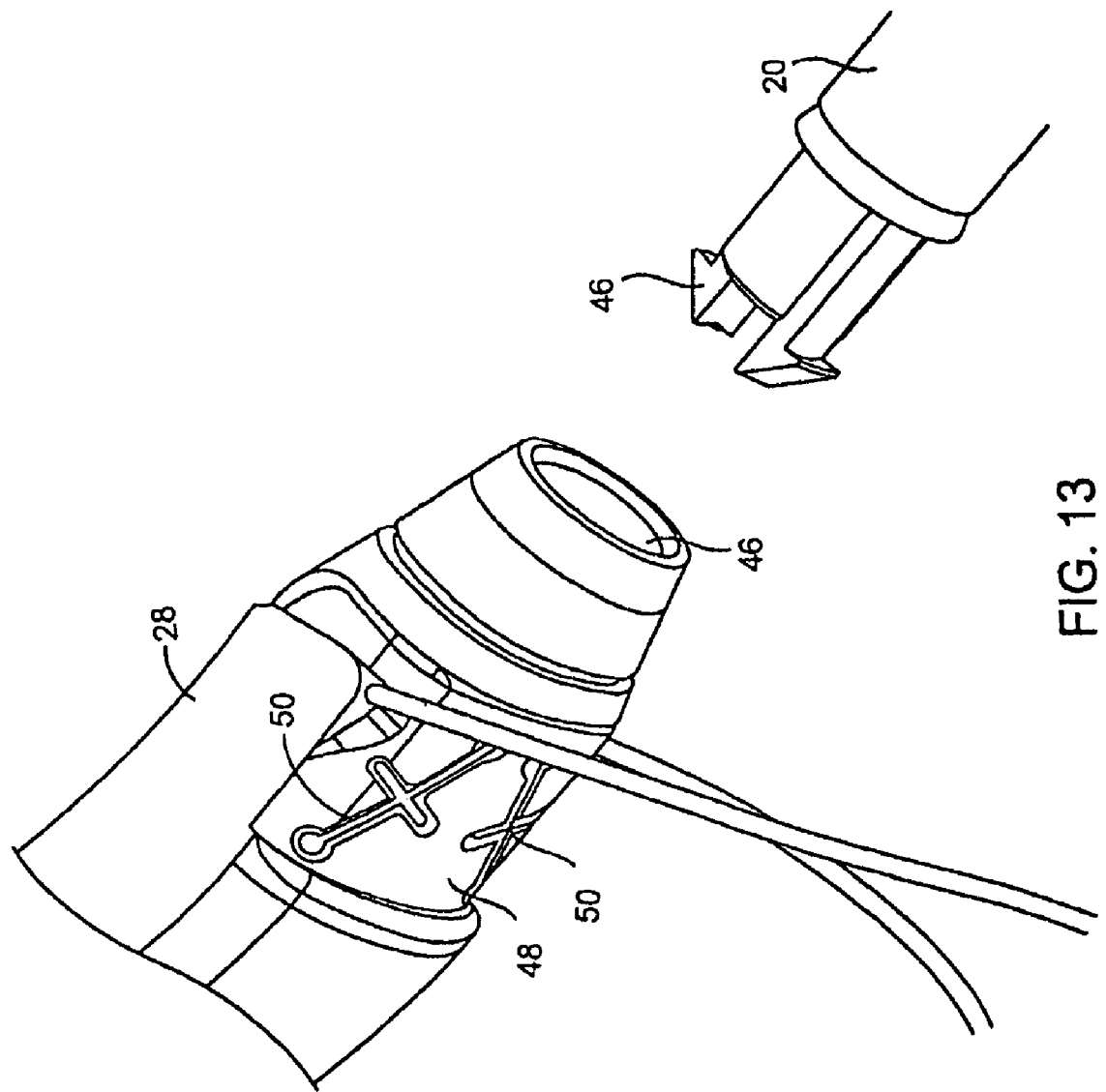
FIG. 13 is an expanded view of the connection between the introducer and the ablation device.

After the appropriate size of ablation device 14 is identified, for example by using introducer 20 as described above, ablation device 14 may be coupled to the proximal end of introducer 20 with any suitable connection, such as mating snap fit connectors 46 as shown in FIGS. 9 and 13. It should be understood that the appropriate size of ablation device 14 may also be determined using a device or method independent of introducer 20. As described above, ablation device 14 is preferably introduced into the patient while straightened, optionally through the use of a sheath. Introducer 20 is then pulled further, as shown in FIGS. 10 and 11, in order to manipulate ablation device 14 and wrap ablation device 14 about the pulmonary veins. As described above, once ablation device 14 has been introduced through the incision, the sheath may be removed in order to permit ablation device 14 to resume its predetermined curvature for manipulation about the pulmonary veins.

Figure 12:
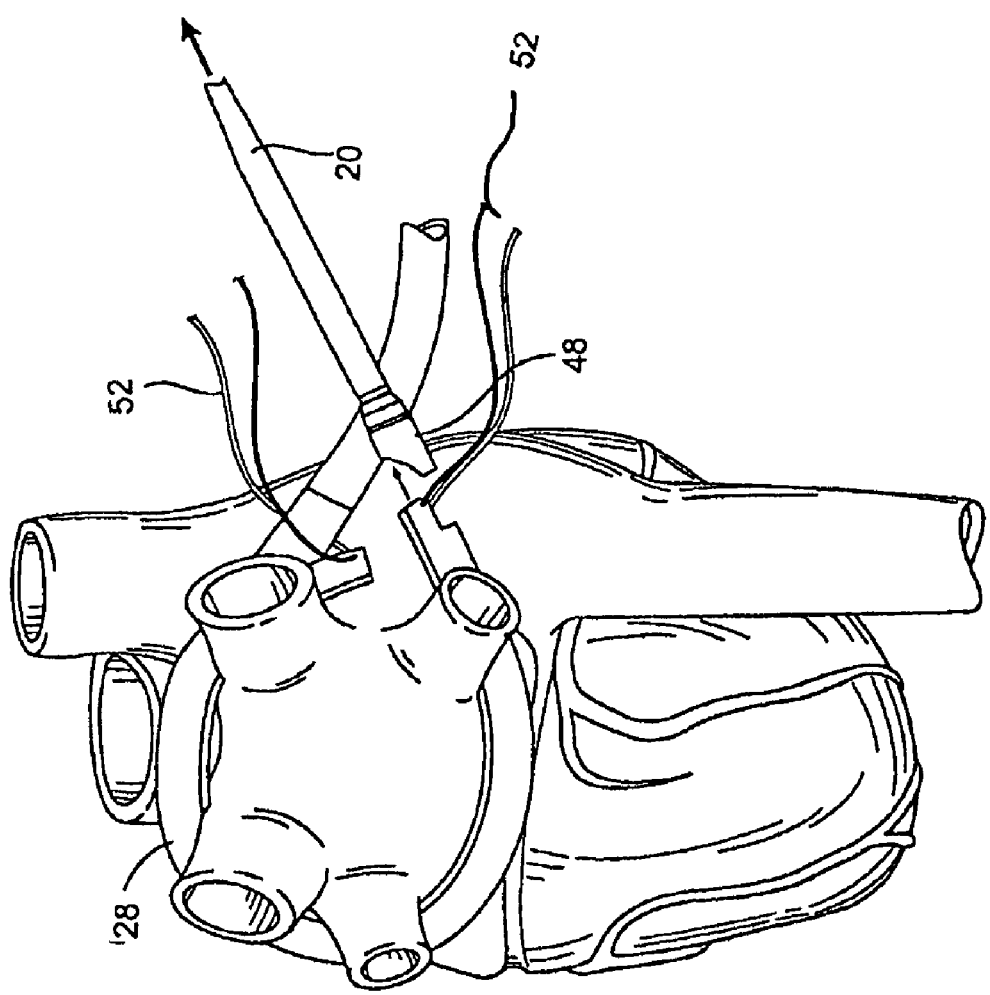
FIG. 12 shows the introducer being decoupled from the ablation device.

As shown in FIG. 12, once ablation device 14 is wrapped about the pulmonary veins, introducer 20 may be detached from ablation device 14 by detaching a releasable assembly 48 from ablation device 14. In some embodiments of the invention, releasable assembly 48 is detached by simply cutting one or more sutures 50 (FIG. 13) that hold releasable assembly 48 to the device 14. It is also contemplated that snap fit connection 46 between introducer 20 and ablation device 14 may be releasable to permit decoupling introducer 20 at the same place introducer 20 is initially coupled to ablation device 24 without the need to cut one or more sutures 50.

Ablation device 14 may then be locked to itself in a third, substantially closed-loop configuration to encircle all or part of the pulmonary veins. Device 14 has elongate elements, such as sutures 52, at both ends, which can be tensioned and cinched together to lock the ends of device 14 to each other using tourniquets 54 and suture snares 56 as shown in FIGS. 6, 14, and 15.

Preferably, ablation device 14 has two opposing pairs of sutures 52, though other numbers and configurations of sutures 52 are regarded as within the scope of the invention.

Sutures 52 are tensioned using tourniquets 54 to approximate the ends of ablation device 14, such that tensioning sutures 52 forces the ends of ablation device 14 together. The sizing of ablation device 14 (which may be determined using introducer 20, as described above) provides a snug fit around all or part of the pulmonary veins such that tensioning sutures 52 forces ablation device 14 into contact with the epicardial surface. Hemostats 58 or other suitable devices may be used to pinch or crimp tourniquets 54 in order to secure ablation device 14 in place about the pulmonary veins as seen in FIG. 15. Alternatively, ablation device 14 may utilize a locking mechanism, such as a buckle or other releasable locking mechanism, to be locked to itself and thereby secured in place about the pulmonary veins.

Ablation device 14 may also contain a suction well to assist device 14 in adhering to the tissue to be ablated. The suction well may take any form, and is preferably formed between the inner and outer lips of body 28 of ablation device 14. The suction well may have a suction port coupled to a vacuum source through a lumen. The vacuum source may be activated to cause the suction well to hold ablation element 26 against the tissue to be ablated. The suction port preferably has a cross-sectional size that is no more than about 10% of the cross-sectional size of the lumen. Thus, if suction is lost at one ablation element 26, suction can be maintained at other ablation elements 26, since the relatively small suction port produces low flow. Of course, another part of the vacuum flow path, other than the suction port, may be sized small to reduce losses through ablation elements 26 not adhered to the tissue.

Controller 12 preferably activates ablation elements 26 in a predetermined manner. The phrase "predetermined manner" is intended to refer to a non-random sequence. In one mode of operation, ablation is carried out at adjacent ablation elements 26. Ablation may also be carried out at a number of pairs of adjacent ablation elements 26, such as the first and second ablation elements 26 and the fifth and sixth ablation elements 26. After ablation is carried out at these adjacent ablation elements 26, another pair or pairs of adjacent ablation elements 26 are activated, such as the third and fourth and seventh and eighth ablation elements 26. The continuity of the ablation between adjacent ablation elements 26 may be confirmed in any suitable manner. In other modes of operation, controller 12 may energize every other ablation element 26, every third ablation element 26, or a limited number of ablation elements 26, such as no more than four. Controller 12 may also activate less than about 50%, and even less than about 30%, of the total ablation area at one time (for ablation device 14, a percentage of the total ablation area is effectively a percentage of the total number of ablation elements 26).

Preferably, ablation device 14 is designed to achieve and maintain particular near surface (NS) temperatures during an ablation procedure. For example, ablation device 14 may be designed to maintain a near surface (NS) temperature of about 0 degree C. to about 80 degrees C., more preferably about 20 degrees C. to about 80 degrees C., and most preferably about 40 degrees C. to about 80 degrees C. The temperature can be adjusted by changing the flow rate of the flowable material, the temperature of the flowable material, and/or the power delivered to ablation elements 26.

In some embodiments, ablation is controlled based on temperature measured by the temperature sensors. For example, controller 12 may incorporate a multiplexer that delivers ablating energy only to those ablation elements 26 having a temperature below a threshold temperature. Alternatively, the multiplexer may deliver ablating energy only to the coldest ablation elements 26 or only to those ablation elements registering the coolest temperatures.

After measuring the temperature change over time, the temperature response may be analyzed to determine the appropriate ablation technique. The analysis may be a comparison of the temperature response to temperature response curves of known tissue types. The temperature response curves may be developed empirically or may be calculated. The temperature response may also consider other variables input by the user, including, but not limited to, blood temperature, blood flow rate, and the presence and amount of fat. When assessing the temperature response during heating with ablation elements 26, the amount of energy delivered to the tissue may also be taken into account in characterizing the tissue.

Using the results of the temperature response assessment, controller 12 preferably determines the appropriate ablation technique to produce the desired far surface (FS) temperature. In one mode of operation, controller 12 determines the amount of time required to reach a desired FS temperature when the NS is maintained at a temperature of less than about 60 degrees C. Controller 12 preferably maintains an adequate flow rate and temperature of the flowable material to maintain the desired NS temperature. Controller 12 monitors the temperature of the NS with the temperature sensors. After the calculated amount of time has elapsed, controller 12 automatically stops delivering ablating energy to ablation elements 26. Alternatively, the ablation may take place until the NS reaches a target temperature as sensed by the temperature sensors. The continuity of the ablation may then be checked in any manner described herein.

Ablation device 14 preferably delivers ultrasound energy focused in at least one dimension. In particular, ablation device 14 preferably delivers focused ultrasound having a focal length of about 2 mm to about 20 mm, more preferably of about 2 mm to about 12 mm, and most preferably of about 8 mm. Stated another way, a focus is spaced apart from a bottom (or contact) surface of ablation device 14 along a focal axis (FA) within the stated ranges. The focused ultrasound also forms an angle of about 10 degrees to about 170 degrees, more preferably of about 30 degrees to about 90 degrees, and most preferably of about 60 degrees relative to the FA. Preferably, a piezoelectric transducer is utilized as an ultrasonic ablation element 26. The transducer is preferably mounted within a housing having an enclosure and a top that fits over the enclosure. The enclosure may have curved lips on both sides of the enclosure that generally conform to the curvature of the transducer. The transducer preferably has a length of about 0.43 inch, a width of about 0.35 inch, and a thickness of about 0.017 inch. The transducer has a radius of curvature (R) consistent with the preferred focal lengths described above. The transducer forms an angle (A) with the focus (F) within the preferred angle ranges described above.

An advantage of using focused ultrasonic energy is that the energy can be concentrated within the tissue. Another advantage of using focused ultrasound is that the energy diverges after reaching the focus, thereby reducing the possibility of damaging tissue beyond the target tissue as compared to collimated ultrasonic energy. When ablating epicardial tissue with collimated ultrasound, the collimated ultrasound energy not absorbed by the target tissue travels through the heart chamber and remains concentrated on a relatively small area when it reaches the endocardial surface on the other side of the chamber. The present invention reduces the likelihood of damage to other structures since the ultrasonic energy diverges beyond the focus and is spread over a larger area.

Although the focused ultrasonic energy is preferably produced with a curved transducer, the focused ultrasonic energy may be produced with any suitable structure. For example, acoustic lensing may be used to provide focused ultrasound. The acoustic lens can be used with a flat piezoelectric element and matching layer. Furthermore, although the ultrasound energy is preferably emitted directly toward the tissue, the ultrasound energy may also be reflected off a surface and directed toward the tissue without departing from the scope of the invention.

The energy may also be produced by a number of small transducers oriented to focus or concentrate ultrasonic energy, such as at least about 90% of the energy, within the preferred angle ranges and radius of curvature described herein when viewed along a longitudinal axis or along the FA. For example, a multi-element acoustic phased array may be used to provide an acoustic beam-steering capability from one or more cells. One skilled in the art can also appreciate the use of multiple matching layers, focusing acoustic lenses, and non-focusing acoustic windows and the like. Thus, the focused energy may be produced in a number of different ways, including other ways not mentioned here, without departing from the scope of the invention.

In another aspect of the invention, ablation device 14 is operated during two different time periods while varying at least one characteristic of ablation device 14, such as the frequency of the ablating energy, the power of the ablating energy, the position of the focus relative to the tissue, and/or the ablating time. For example, ablation device 14 may be operated at varying frequencies over time to ablate tissue in a controlled manner. Specifically, ablation device 14 is preferably operated to create a transmural lesion by controlling the delivery of energy to the tissue. Although it is preferred to vary the frequency when ablating the tissue, ablation device 14 may, of course, be operated at a single frequency without departing from the spirit and scope of the invention.

In a first treatment method of the present invention, the transducer is activated at a frequency of about 2 MHz to about 7 MHz, and preferably of about 3.5 MHz, and a power of about 80 watts to about 150 watts, and preferably of about 130 watts, in short bursts. For example, the transducer may be activated for about 0.01 second to about 2.0 seconds, and preferably for about 1.2 seconds. The transducer is inactive for about 2 seconds to about 90 seconds, more preferably about 5 seconds to about 80 seconds, and most preferably about 45 seconds between activations. In this manner, a controlled amount of accumulated energy can be delivered to the tissue in short bursts to heat tissue at and near the focus while minimizing the impact of blood cooling at the FS. Ablation at this frequency may continue until a controlled amount of energy is delivered, such as about 0.5 kilojoule to about 3 kilojoules. Treatment at this frequency in relatively short bursts produces localized heating at the focus. At the first frequency, energy is not absorbed as quickly in the tissue as it is at higher frequencies, so that heating at the focus is not significantly affected by absorption of ultrasound energy in tissue before reaching the focus.

Following treatment at the first frequency, the transducer is operated for longer periods of time, preferably about 1 second to about 4 seconds, and more preferably about 2 seconds, to ablate tissue between the focus and the transducer. The frequency during this treatment is also preferably about 2 MHz to about 14 MHz, more preferably about 3 MHz to about 7 MHz, and most preferably about 6 MHz. The transducer is operated for about 0.7 second to about 4 seconds at a power of about 20 watts to about 80 watts, and preferably about 60 watts. The transducer is inactive for between about 3 seconds and about 60 seconds, and preferably for about 40 seconds, between each activation. In this manner, a controlled amount of energy can be delivered to heat tissue between the focus and the transducer. The treatment at this frequency may continue until a controlled amount of total energy is delivered, such as about 750 joules.

As a final treatment, the ultrasonic transducer is activated at a higher frequency to heat and ablate the NS. The transducer is preferably operated at a frequency of between about 3 MHz and about 16 MHz, and preferably at about 6 MHz. The transducer is operated at lower power than the treatment methods above since the ultrasonic energy is rapidly absorbed by the tissue at these frequencies, so that the NS is heated quickly. In a preferred method, the transducer is operated at about 2 watts to about 20 watts, and more preferably about 15 watts. The transducer is preferably operated for a sufficient duration to ablate tissue, such as about 20 seconds to about 80 seconds, and preferably about 40 seconds. Often, the NS temperature will reach about 70 degrees C. to about 85 degrees C.

Each of the treatments described above may be used by itself or in combination with other treatments. Furthermore, the combination of transducer size, power, frequency, activation time, and focal length may all be varied to produce the desired delivery of ultrasound energy to the tissue. As such, it is understood that the preferred embodiment may be adjusted by adjusting one or more of the characteristics and, thus, these parameters may be changed without departing from the spirit and scope of the invention. The treatment sequence described above generally delivers energy closer to the NS during the second treatment and even closer to the NS for the third treatment (that is, it ablates tissue from the FS towards the NS in successive treatments).

The focus of the ultrasound energy may also be moved relative to the tissue to deliver energy to different depths in the tissue. Ablation device 14 can be moved closer to and farther away from the target tissue, with membrane 40 conforming to the required shape to fill the gap between the transducer and the tissue. Membrane 40 is preferably inflated, for example utilizing a fluid such as saline, and deflated to move the focus. However, ablation device 14 may also be moved with any other suitable mechanism, such as a threaded foot.

The focus may be moved while ablation elements 26 are activated or may be moved between activations of ablation elements 26. Moving the focus of the ultrasound energy may be sufficient to create a transmural lesion without changing frequencies, or may be used in conjunction with a change in frequencies as described above. The focus may also be moved in any other manner such as with a phased array or variable acoustic lensing.

After ablation elements 26 have been activated to ablate tissue, it may be necessary to ablate tissue in gaps between ablations from each ablation element 26. In one method of ablating these gaps, the entire ablation device 14 is shifted so that at least some ablation elements 26 are positioned to ablate tissue within one or more gaps. Thus, after first ablating tissue with all of the ablation elements 26, ablation device 14 is shifted and at least some, and preferably all, ablation elements 26 are activated again to create a substantially continuous lesion.

Another method to ablate tissue within gaps is to tilt ablation elements 26 to ablate tissue within gaps. In this method, ablation device 14 does not need to be moved. Rather, membrane 40 may be inflated to tilt the transducer, which directs the ultrasound energy toward tissue within gaps between transducers.

In another embodiment, ablation elements 26 may be located along a track such that one or more ablation elements 26 may be adjusted or moved (for example, by sliding) along the track so that any gaps in the ablation may be filled in by an activation of ablation elements 26 after they have been resituated over any such gaps. The use of sliding elements 26 may also be used to reduce the number of overall ablation elements 26 that are needed for an ablation procedure. For example, if sizing measurements (e.g., with introducer 20) reveal that an appropriately sized ablation device 14 would require 20 ablation elements 26, an ablation device 14 having 10 or fewer ablation elements 26 could be used, provided the 10 ablation elements 26 are adjustable along the track in order to complete the ablation annulus. Preferably, the track could be made using a superelastic material, including for example, a memory metal such as Nitinol. For example, all of the ablation elements 26 may be interconnected using one or more tracks of Nitinol or another superelastic material, such that ablation device 14 may be straightened for insertion into a patient and thereafter manipulated into a predetermined curvature to facilitate manipulations around the heart.

When the track is formed of superelastic material, the track not only permits ablation elements 26 to move therealong, it also permits ablation device 14 to achieve two different configurations. As described above, the superelastic properties allow ablation device 14 to be deformed such that ablation elements 26 are substantially coplanar, thereby allowing ablation device 14 to be straightened for insertion and guiding through a small incision, and then returning to the predetermined curvature when manipulated about the heart.

The track itself, or an isolated channel in the track, may also permit transmission of control signals from controller 12 that are used to control the operation of ablation elements 26 positioned along the track. These control signals may be used to reposition ablation elements 26 along the trap or otherwise alter the ablating energy being delivered to the tissue.

Controller 12 may be designed to automatically ablate in any manner described herein. For example, controller 12 can change the frequency, power, focal length, and/or operating time to provide the desired ablating technique. The change in frequency and power may be completely automatic or may require some user input such as visual indications of fat and/or tissue thickness. For example, controller 12 may be designed to automatically sequence through two or more different ablating techniques such as those described above. Other techniques, of course, may be used depending on the tissue characteristics and the type and characteristics of the one or more ultrasound transducers. Controller 12 may also utilize feedback, such as temperature feedback or electrical impedance, to actively control the ablations.

Once the PV isolation ablation lesion has been created, for example using ablation device 14 as described above, a second ablation device, such as ablation device 70 illustrated in FIGS. 17-21, may be introduced in order to create the mitral isthmus ablation lesion. Ablation device 70 generally includes an elongate, flexible body, such as strap 72, and at least one movable ablation element 74, preferably incorporated into a two-element array. Ablation elements 74 may be any type of ablation element, including, but not limited to, RF ablation elements, ultrasound ablation elements, laser ablation elements, cryogenic ablation elements, and microwave ablation elements. One or more conduction wires 76 couple ablation elements 74 to a suitable source of ablation energy, which may be incorporated within or separate from controller 12.

Similar to ablation device 14, ablation device 70 may be introduced in a substantially flat configuration, manipulated about the heart in a generally curved configuration, and then locked to itself in a configuration encircling all or part of one or more of the pulmonary veins. Accordingly, ablation device 70 may incorporate one or more features described in connection with ablation device 14, such as snap fit connection 46, releasable assembly 48, or sutures 52.

In order to facilitate creation of contiguous lesions, ablation device 70 is preferably positioned to overlap the PV isolation ablation created by ablation device 14. In some embodiments of the invention, ablation device 70 may be releasably coupled to the trailing edge of ablation device 14 such that, as ablation device 14 is removed from the patient, ablation device 70 is introduced into the patient in much the same way as ablation device 14 is introduced into the patient as introducer 20 is removed. However, ablation device 70 may be introduced into the patient in any other fashion without departing from the spirit and scope of the present invention.

Figure 20:
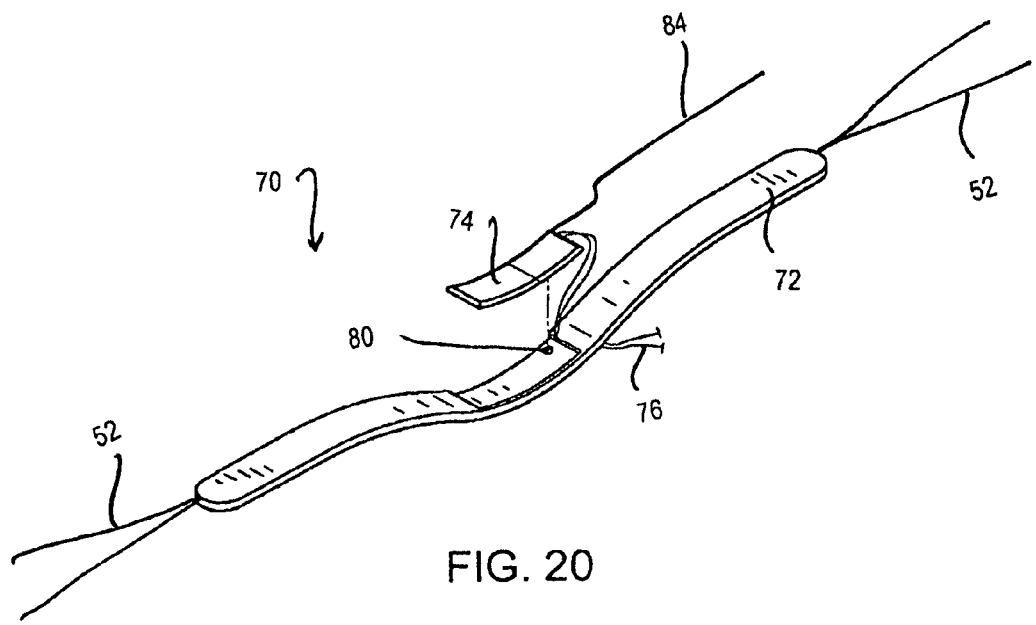
FIG. 20 is an exploded top view of the ablation device of FIG. 17.
Figure 21:
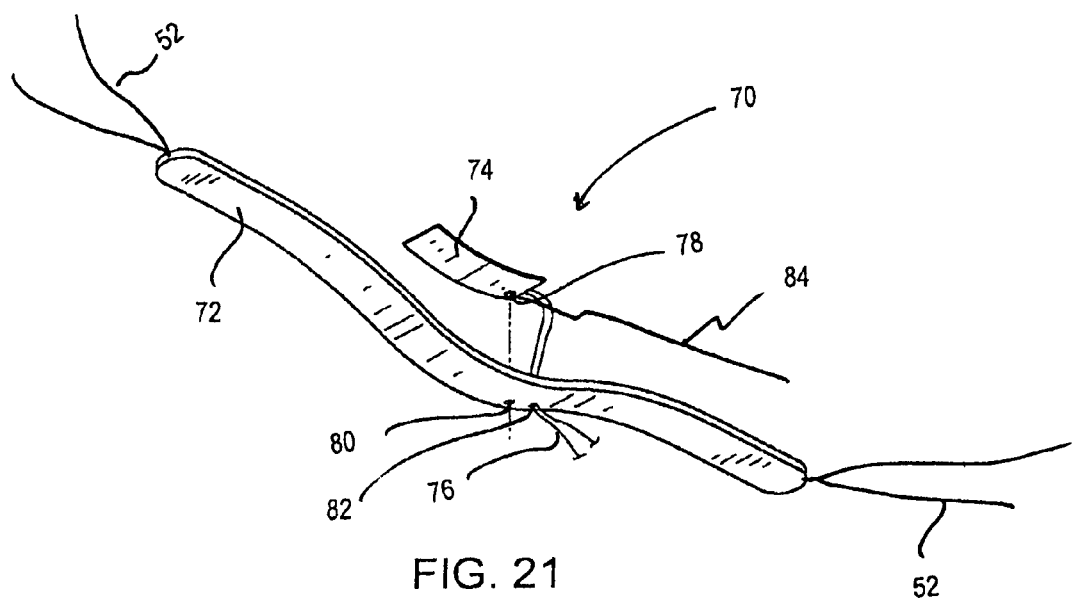
FIG. 21 is an exploded bottom view of the ablation device of FIG. 17.

As shown in FIGS. 20 and 21, movable ablation elements 74 are coupled to strap 72 via a pivot pin 78 depending from the underside of movable ablation elements 74. Pivot pin 78 mates with a pivot hole 80 in strap 72. A through hole 82 may be provided as a channel for wires 76, though wires 76 may also extend internal to strap 72 without departing from the spirit and scope of the present invention. In order to manipulate movable ablation elements 74 off the axis of ablation device 70, one or more control cables 84 may be coupled thereto in such a manner as to pivot movable ablation elements 74 (e.g., by tensioning and releasing tension on cable 84). Alternatively, an additional introducer, strap, or formed stylus could be employed to deploy movable ablation elements 74.

Figure 19:
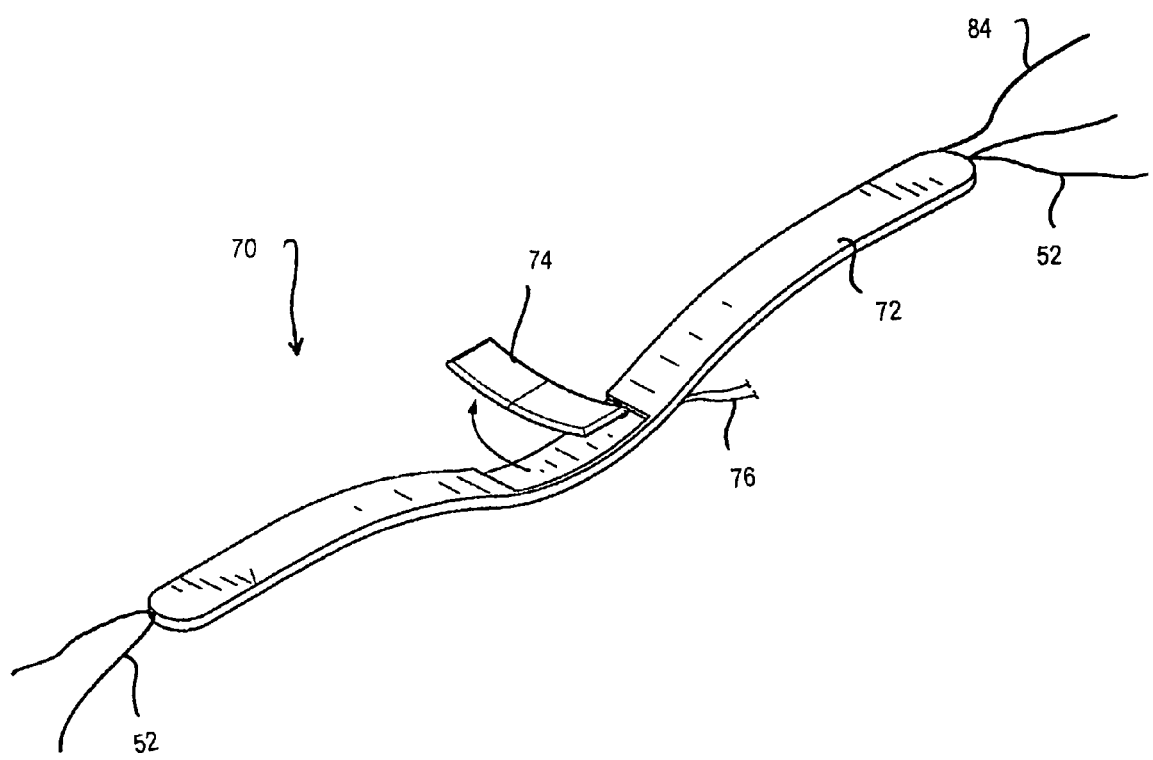
FIG. 19 illustrates the ablation device of FIG. 17 with the ablation elements deployed in a substantially orthogonal configuration.

Once ablation device 70 is properly positioned, movable ablation elements 74 may be rotated, pivoted, or otherwise deployed into a position off the axis of ablation device 70. That is, movable ablation elements 74 may be adjusted into a position forming an angle relative to a longitudinal axis of ablation device 70. The angle is preferably between about zero degrees and about ninety degrees. For example, movable ablation elements 74 may be deployed perpendicular to the line encircling the pulmonary veins in order to create the mitral isthmus ablation or another linear ablation, and then activated to deliver ablation energy to the tissue. As shown in FIG. 19, movable ablation elements 74 pivot about pivot pin 78. Since ablation device 70 is preferably positioned to overlap the PV isolation lesion created by ablation device 14, movable ablation elements 74 retain substantial continuity with the PV isolation lesion even when deployed. This permits precise and contiguous placement of linear lesions relative to the PV isolation lesion. Further, since ablation device 70 is preferably secured to itself, thereby exerting a moderate compressive force on the heart, linear lesions are properly placed even on a beating heart.

Although a perpendicular deployment is illustrated in FIG. 19, it should be understood that any other orientation, between about zero degrees and about 180 degrees, may also be achieved and utilized in creating linear lesions using ablation device 70. Additionally, the location of pivot pin 78 and pivot hole 80 may be adjusted to provide additional configurations.

Figure 22:
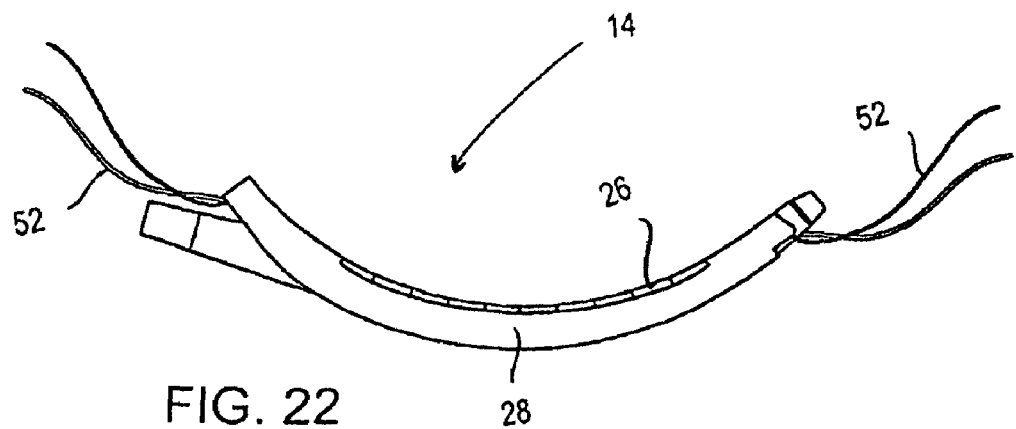
FIG. 22 depicts an ablation device incorporating both fixed and movable ablation elements.
Figure 23:
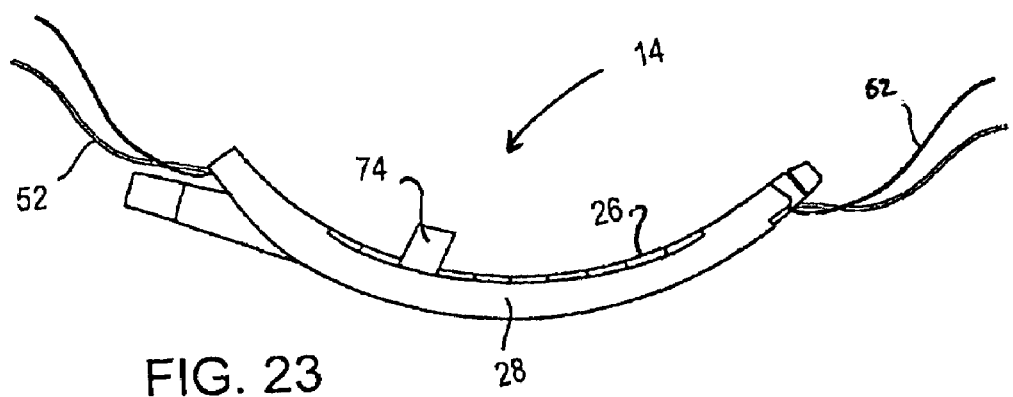
FIG. 23 depicts the ablation device of FIG. 22 with a single ablation element deployed out of the axis of the ablation device.
Figure 24:
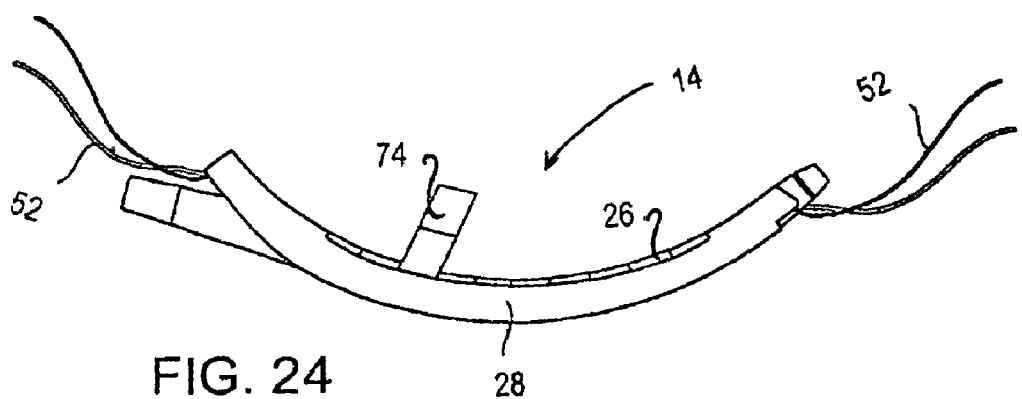
FIG. 24 depicts the ablation device of FIG. 22 with multiple ablation elements deployed out of the axis of the ablation device.

FIGS. 22-24 illustrate that one or more movable ablation elements 74 may be incorporated into ablation device 14, such that a single device may be utilized for both the PV isolation ablation and the mitral isthmus ablation. Such a configuration has the advantage of ensuring that movable ablation elements 74 overlap the PV isolation ablation, thus facilitating a mitral isthmus ablation contiguous with the PV isolation ablation. Further, such a configuration simplifies the surgical procedure by requiring only a single access to the patient's heart.

Although several embodiments of this invention have been described above with a certain degree of particularity, those skilled in the art could make numerous alterations to the disclosed embodiments without departing from the spirit or scope of this invention. For example, although ablation device 14 has been described in connection with creating a substantially continuous lesion around all pulmonary veins, and ablation device 70 described in connection with creating a contiguous mitral isthmus ablation lesion, it should be understood that the methods disclosed herein are equally applicable to ablating only partially around the pulmonary veins. Furthermore, other lesions may be beneficial in treating electrophysiological conditions, and the devices and methods described herein may be useful in creating such lesions on other parts of the heart and in other areas of the body. Additionally, it should be understood that the use of ablation device 14 to create PV isolation ablations is merely exemplary, and that PV isolation ablation may equally well be created with any suitable device. It should also be understood the movable ablation elements described herein may be implemented in a wand-type ablation device as well as the belt-type ablation devices discussed herein, for example in order to both create the mitral isthmus ablation lesion and to fill in gaps in the PV isolation ablation lesion.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A device for ablating tissue, comprising:
    an elongate, flexible body configured to wrap about a cardiac structure, the elongate, flexible body having a first end, a second end, and a longitudinal axis extending from the first end to the second end and at least one of a pair of cooperating structures coupled to one of said first end and said second end; and
    at least one movable ablation element coupled to said body, wherein the elongate, flexible body is formable into a substantially flat configuration in which the elongate, flexible body and the at least one movable ablation element lie in a plane, and a closed loop configuration in which the first end of the elongate, flexible body is secured to the second end of the elongate, flexible body via the pair of cooperating structures,
    wherein said at least one movable ablation element is adjustable relative to said body within the plane to form an angle with the longitudinal axis of said body between about zero degrees and about ninety degrees.

2. The device according to claim 1, wherein said at least one movable ablation element is pivotably coupled to said body.

3. The device according to claim 1, wherein said at least one movable ablation element comprises a two element array.

4. The device according to claim 3, further comprising a pivot pin depending from an underside of said two element array, wherein said pivot pin pivotably connects said two element array to said body via a mating pivot hole in said body.

5. The device according to claim 1, wherein said body is in a generally curved configuration when in a relaxed state.

6. The device according to claim 1, further comprising at least one non-movable ablation element coupled to said body, said at least one non-movable ablation element forming an angle of about zero degrees with the longitudinal axis of said body.

7. The device according to claim 1, further comprising at least one control cable coupled to said at least one movable ablation element and configured to manipulate said at least one movable ablation element into an angled position relative to the longitudinal axis of said body.

8. A method of manufacturing a device for ablating tissue, comprising the steps of:
    providing an elongate, flexible body having a first end, a second end, and a longitudinal axis extending from the first end to the second end, wherein the elongate, flexible body is formable into a substantially flat configuration and a closed loop configuration;
    attaching cooperating first and second locking elements to the first end second ends of the elongate, flexible body, respectively, for securing the first and second ends of the elongate, flexible body to each other in the closed loop configuration;
    providing at least one ablation element; and
    movably coupling the at least one ablation element to the body such that the at least one ablation element lies within a plane of the elongate, flexible body when the elongate, flexible body is in the substantially flat configuration and can be moved within the plane of the elongate flexible body to form an angle of between about zero degrees and about 180 degrees with the longitudinal axis of said body.

* * * * *